(12) United States Patent
Ueda et al.

(10) Patent No.: US 11,499,965 B2
(45) Date of Patent: Nov. 15, 2022

(54) KIT FOR DETECTING ANTIGEN OR MEASURING ITS AMOUNT

(71) Applicant: TOKYO INSTITUTE OF TECHNOLOGY, Tokyo (JP)

(72) Inventors: Hiroshi Ueda, Tokyo (JP); Yuki Ohmuro, Tokyo (JP); Chihiro Miyake, Tokyo (JP); Tomoya Tsukahara, Tokyo (JP)

(73) Assignee: TOKYO INSTITUTE OF TECHNOLOGY, Tokyo (JP)

( * ) Notice: Subject to any disclaimer, the term of this patent is extended or adjusted under 35 U.S.C. 154(b) by 265 days.

(21) Appl. No.: 16/484,376

(22) PCT Filed: Jan. 17, 2018

(86) PCT No.: PCT/JP2018/001186
§ 371 (c)(1),
(2) Date: Aug. 7, 2019

(87) PCT Pub. No.: WO2018/147018
PCT Pub. Date: Aug. 16, 2018

(65) Prior Publication Data
US 2019/0376958 A1 Dec. 12, 2019

(30) Foreign Application Priority Data

Feb. 8, 2017 (JP) .............................. JP2017-021164

(51) Int. Cl.
*G01N 33/542* (2006.01)
*C07K 14/30* (2006.01)

(52) U.S. Cl.
CPC ........... *G01N 33/542* (2013.01); *C07K 14/30* (2013.01)

(58) Field of Classification Search
CPC .... C07K 14/30; G01N 33/542; G01N 33/582; G01N 33/6854
See application file for complete search history.

(56) References Cited

U.S. PATENT DOCUMENTS

| 9,788,776 B1 | 10/2017 | Thompson et al. |
| 2003/0143651 A1 | 7/2003 | Steward et al. |
| 2006/0029946 A1 | 2/2006 | Hahn |
| 2011/0003312 A1 | 1/2011 | Berget |
| 2012/0165204 A1 | 6/2012 | Hahn et al. |
| 2016/0139151 A1 | 5/2016 | Ward et al. |

FOREIGN PATENT DOCUMENTS

| JP | 3462209 B2 | 11/2003 |
| JP | 2005-520000 A | 7/2005 |
| JP | 2006-223195 A | 8/2006 |
| JP | 2007-529718 A | 10/2007 |
| WO | WO 2017/010381 A1 | 1/2017 |

OTHER PUBLICATIONS

Huynh Nhat et al., "Antibody-based fluorescent and fluorescent ratiometric indicators for detection of phosphotyrosine," J. Biosci. Bioeng., 2016, vol. 122, No. 2, pp. 146-154.*
Dong et al., "PM Q-probe: A fluorescent binding protein that converts many antibodies to a fluorescent biosensor," Biosens. Bioelectron., Oct. 1, 2020 ;165:112425. doi: 10.1016/j.bios.2020.112425. Epub Jul. 3, 2020, pp. 1-8.*
International Preliminary Report on Patentability and English translation of the Written Opinion of the International Searching Authority, dated Aug. 22, 2019, for International Application No. PCT/JP2018/001186.
Grover et al.,"A Structurally Distinct Human Mycoplasma Protein that Generically Blocks Antigen-Antibody Union", Science, Feb. 7, 2014, vol. 343, No. 6171, pp. 656-661.
International Search Report (PCT/ISA/210) issued in PCT/JP2018/001186, dated Mar. 27, 2018.
Jeong et al., "One-pot construction of Quenchbodies using antibody-binding proteins", Analytical Methods, Nov. 21, 2016, vol. 8, No. 43, pp. 7774-7779.
Sandin et al., "Isolation and Detection of Human IgA Using a Streptococcal IgA-Binding Peptide", The Journal of Immunology, Aug. 1, 2002, vol. 169, No. 3, pp. 1357-1364.
Written Opinion (PCT/ISA/237) issued in PCT/JP2018/001186, dated Mar. 27, 2018.

* cited by examiner

*Primary Examiner* — Galina M. Yakovleva
(74) *Attorney, Agent, or Firm* — Birch, Stewart, Kolasch & Birch, LLP

(57) ABSTRACT

The purpose of the present invention is to develop a kit capable of detecting antigen or measuring its amount with high sensitivity without requiring an immobilization step and a washing step. The present invention provides a kit for detecting antigen or measuring its amount. The kit comprises a complex of a polypeptide including an antibody light chain variable region and a polypeptide including an antibody heavy chain variable region and a protein M fragment labeled with a fluorescent dye. The protein M fragment is a fragment having a binding ability to the complex.

4 Claims, 10 Drawing Sheets
Specification includes a Sequence Listing.

Fig.1
Fig.2
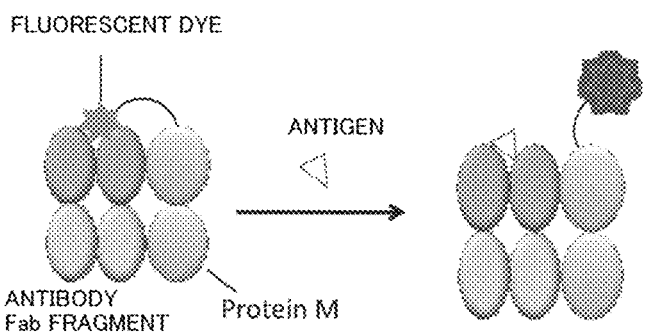
Fig.3
① 5' [TrxA' | H₆ | Protein M | (SGGG)₂ | Cys] 3'
② 5' [TrxA | H₆ | Protein M | (SGGG)₂ | Cys] 3'
③ 5' [TrxA' | H₆ | Protein M | C term | (SGGG)₂ | Cys] 3'
④ 5' [TrxA | H₆ | Protein M | C term | (SGGG)₂ | Cys] 3'
\* TrxA': Trx w/o Cys PMdQ

PM-Q dPMdQ dPM-Q

SEQUENCE LISTING

<160> NUMBER OF SEQ ID NOS: 17

<210> SEQ ID NO 1
<211> LENGTH: 556
<212> TYPE: PRT
<213> ORGANISM: Mycoplasma genitalium

<400> SEQUENCE: 1

```
Met Gln Phe Lys Lys His Lys Asn Ser Val Lys Phe Lys Arg Lys Leu
1               5                   10                  15

Phe Trp Thr Ile Gly Val Leu Gly Ala Gly Ala Leu Thr Thr Phe Ser
            20                  25                  30

Ala Val Met Ile Thr Asn Leu Val Asn Gln Ser Gly Tyr Ala Leu Val
        35                  40                  45

Ala Ser Gly Arg Ser Gly Asn Leu Gly Phe Lys Leu Phe Ser Thr Gln
    50                  55                  60

Ser Pro Ser Ala Glu Val Lys Leu Lys Ser Leu Ser Leu Asn Asp Gly
65                  70                  75                  80
```

```
Ser Tyr Gln Ser Glu Ile Asp Leu Ser Gly Gly Ala Asn Phe Arg Glu
                85                  90                  95

Lys Phe Arg Asn Phe Ala Asn Glu Leu Ser Glu Ala Ile Thr Asn Ser
            100                 105                 110

Pro Lys Gly Leu Asp Arg Pro Val Pro Lys Thr Glu Ile Ser Gly Leu
            115                 120                 125

Ile Lys Thr Gly Asp Asn Phe Ile Thr Pro Ser Phe Lys Ala Gly Tyr
            130                 135                 140

Tyr Asp His Val Ala Ser Asp Gly Ser Leu Leu Ser Tyr Tyr Gln Ser
145                 150                 155                 160

Thr Glu Tyr Phe Asn Asn Arg Val Leu Met Pro Ile Leu Gln Thr Thr
                165                 170                 175

Asn Gly Thr Leu Met Ala Asn Asn Arg Gly Tyr Asp Asp Val Phe Arg
            180                 185                 190

Gln Val Pro Ser Phe Ser Gly Trp Ser Asn Thr Lys Ala Thr Thr Val
            195                 200                 205

Ser Thr Ser Asn Asn Leu Thr Tyr Asp Lys Trp Thr Tyr Phe Ala Ala
            210                 215                 220

Lys Gly Ser Pro Leu Tyr Asp Ser Tyr Pro Asn His Phe Phe Glu Asp
225                 230                 235                 240

Val Lys Thr Leu Ala Ile Asp Ala Lys Asp Ile Ser Ala Leu Lys Thr
                245                 250                 255

Thr Ile Asp Ser Glu Lys Pro Thr Tyr Leu Ile Ile Arg Gly Leu Ser
            260                 265                 270

Gly Asn Gly Ser Gln Leu Asn Glu Leu Gln Leu Pro Glu Ser Val Lys
            275                 280                 285

Lys Val Ser Leu Tyr Gly Asp Tyr Thr Gly Val Asn Val Ala Lys Gln
            290                 295                 300

Ile Phe Ala Asn Val Val Glu Leu Glu Phe Tyr Ser Thr Ser Lys Ala
305                 310                 315                 320

Asn Ser Phe Gly Phe Asn Pro Leu Val Leu Gly Ser Lys Thr Asn Val
                325                 330                 335

Ile Tyr Asp Leu Phe Ala Ser Lys Pro Phe Thr His Ile Asp Leu Thr
            340                 345                 350

Gln Val Thr Leu Gln Asn Ser Asp Asn Ser Ala Ile Asp Ala Asn Lys
            355                 360                 365

Leu Lys Gln Ala Val Gly Asp Ile Tyr Asn Tyr Arg Arg Phe Glu Arg
            370                 375                 380

Gln Phe Gln Gly Tyr Phe Ala Gly Gly Tyr Ile Asp Lys Tyr Leu Val
385                 390                 395                 400

Lys Asn Val Asn Thr Asn Lys Asp Ser Asp Asp Leu Val Tyr Arg
                405                 410                 415

Ser Leu Lys Glu Leu Asn Leu His Leu Glu Glu Ala Tyr Arg Glu Gly
            420                 425                 430

Asp Asn Thr Tyr Tyr Arg Val Asn Glu Asn Tyr Pro Gly Ala Ser
            435                 440                 445

Ile Tyr Glu Asn Glu Arg Ala Ser Arg Asp Ser Glu Phe Gln Asn Glu
            450                 455                 460

Ile Leu Lys Arg Ala Glu Gln Asn Gly Val Thr Phe Asp Glu Asn Ile
465                 470                 475                 480

Lys Arg Ile Thr Ala Ser Gly Lys Tyr Ser Val Gln Phe Gln Lys Leu
                485                 490                 495
```

-continued

```
Glu Asn Asp Thr Asp Ser Ser Leu Glu Arg Met Thr Lys Ala Val Glu
                500                 505                 510
Gly Leu Val Thr Val Ile Gly Glu Glu Lys Phe Glu Thr Val Asp Ile
            515                 520                 525
Thr Gly Val Ser Ser Asp Thr Asn Glu Val Lys Ser Leu Ala Lys Glu
        530                 535                 540
Leu Lys Thr Asn Ala Leu Gly Val Lys Leu Lys Leu
545                 550                 555

<210> SEQ ID NO 2
<211> LENGTH: 1190
<212> TYPE: DNA
<213> ORGANISM: Mycoplasma genitalium
<220> FEATURE:
<221> NAME/KEY: CDS
<222> LOCATION: (9)..(1181)

<400> SEQUENCE: 2 ccatgggt aat gat ggt agc tat cag agc gaa att gat ctg agc ggt ggt      50
         Asn Asp Gly Ser Tyr Gln Ser Glu Ile Asp Leu Ser Gly Gly
          1               5                  10 gca aat ttt cgt gaa aaa ttt cgc aac ttt gcc aac gaa ctg agc gaa      98
Ala Asn Phe Arg Glu Lys Phe Arg Asn Phe Ala Asn Glu Leu Ser Glu
 15                  20                  25                  30 gca att acc aat agc ccg aaa ggt ctg gat cgt ccg gtt ccg aaa acc     146
Ala Ile Thr Asn Ser Pro Lys Gly Leu Asp Arg Pro Val Pro Lys Thr
                 35                  40                  45 gaa att tca ggt ctg att aaa acg ggt gat aac ttt att acc ccg tcc     194
Glu Ile Ser Gly Leu Ile Lys Thr Gly Asp Asn Phe Ile Thr Pro Ser
             50                  55                  60 ttt aaa gcc ggt tat tac gat cat gtt gca tca gat ggt agc ctg ctg     242
Phe Lys Ala Gly Tyr Tyr Asp His Val Ala Ser Asp Gly Ser Leu Leu
         65                  70                  75 agc tat tat cag agc acc gaa tat ttc aat aat cgt gtg ctg atg ccg     290
Ser Tyr Tyr Gln Ser Thr Glu Tyr Phe Asn Asn Arg Val Leu Met Pro
     80                  85                  90 att ctg cag acc acc aat ggc acc ctg atg gca aat aat cgc ggt tat     338
Ile Leu Gln Thr Thr Asn Gly Thr Leu Met Ala Asn Asn Arg Gly Tyr
 95                 100                 105                 110 gat gat gtt ttt cgt cag gtg ccg agc ttt agc ggt tgg agc aat acc     386
Asp Asp Val Phe Arg Gln Val Pro Ser Phe Ser Gly Trp Ser Asn Thr
                115                 120                 125 aaa gca acc acc gtt agc acc agc aat aat ctg acc tat gat aaa tgg     434
Lys Ala Thr Thr Val Ser Thr Ser Asn Asn Leu Thr Tyr Asp Lys Trp
            130                 135                 140 acc tac ttt gca gca aaa ggt agt ccg ctg tat gat agt tat ccg aac     482
Thr Tyr Phe Ala Ala Lys Gly Ser Pro Leu Tyr Asp Ser Tyr Pro Asn
        145                 150                 155 cac ttt ttt gag gac gtt aaa acc ctg gca att gat gcc aaa gat att     530
His Phe Phe Glu Asp Val Lys Thr Leu Ala Ile Asp Ala Lys Asp Ile
    160                 165                 170 agc gca ctg aaa acc acc att gat agc gaa aaa ccg acc tat ctg att     578
Ser Ala Leu Lys Thr Thr Ile Asp Ser Glu Lys Pro Thr Tyr Leu Ile
175                 180                 185                 190 att cgt ggt ctg agt ggt aat ggt agt cag ctg aat gaa ctg cag ctg     626
Ile Arg Gly Leu Ser Gly Asn Gly Ser Gln Leu Asn Glu Leu Gln Leu
                195                 200                 205 ccg gaa agc gtt aaa aaa gtt agc ctg tat ggt gat tat acg ggt gtt     674
Pro Glu Ser Val Lys Lys Val Ser Leu Tyr Gly Asp Tyr Thr Gly Val
            210                 215                 220
```

-continued

| | | |
|---|---|---|
| aat gtg gcc aaa caa att ttt gcc aat gtg gtc gaa ctg gaa ttt tac<br>Asn Val Ala Lys Gln Ile Phe Ala Asn Val Val Glu Leu Glu Phe Tyr<br>225 230 235 | | 722 |
| agc acc agt aaa gca aac agc ttt ggt ttt aat ccg ctg gtt ctg ggt<br>Ser Thr Ser Lys Ala Asn Ser Phe Gly Phe Asn Pro Leu Val Leu Gly<br>240 245 250 | | 770 |
| agc aaa acc aat gtt att tat gac ctg ttt gcc agc aaa ccg ttt acc<br>Ser Lys Thr Asn Val Ile Tyr Asp Leu Phe Ala Ser Lys Pro Phe Thr<br>255 260 265 270 | | 818 |
| cat atc gat ctg acc cag gtt acc ctg cag aat agc gat aat agc gcc<br>His Ile Asp Leu Thr Gln Val Thr Leu Gln Asn Ser Asp Asn Ser Ala<br>275 280 285 | | 866 |
| att gat gca aac aaa ctg aaa cag gca gtt ggc gat att tac aac tat<br>Ile Asp Ala Asn Lys Leu Lys Gln Ala Val Gly Asp Ile Tyr Asn Tyr<br>290 295 300 | | 914 |
| cgt cgt ttt gaa cgt cag ttc cag ggt tat ttt gcc ggt ggt tat atc<br>Arg Arg Phe Glu Arg Gln Phe Gln Gly Tyr Phe Ala Gly Gly Tyr Ile<br>305 310 315 | | 962 |
| gat aaa tat ctg gtg aaa aac gtg aac acc aac aaa gat agt gat gat<br>Asp Lys Tyr Leu Val Lys Asn Val Asn Thr Asn Lys Asp Ser Asp Asp<br>320 325 330 | | 1010 |
| gat ctg gtt tat cgc agc ctg aaa gaa ctg aat ctg cat ctg gaa gag<br>Asp Leu Val Tyr Arg Ser Leu Lys Glu Leu Asn Leu His Leu Glu Glu<br>335 340 345 350 | | 1058 |
| gca tat cgt gaa ggt gat aat acc tat tat cgt gtg aac gag aac tat<br>Ala Tyr Arg Glu Gly Asp Asn Thr Tyr Tyr Arg Val Asn Glu Asn Tyr<br>355 360 365 | | 1106 |
| tat ccc ggg gca agc att tat gaa aat gaa cgt gca agc cgt gat agc<br>Tyr Pro Gly Ala Ser Ile Tyr Glu Asn Glu Arg Ala Ser Arg Asp Ser<br>370 375 380 | | 1154 |
| gag ttt cag aat gaa atc ctg aaa cgt gcgg ccgcc<br>Glu Phe Gln Asn Glu Ile Leu Lys Arg<br>385 390 | | 1190 |

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 3
gagaactatt atccctcagg tgagggagc ggc                     33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 4
ctgaaacgtg cggcctcagg tgagggagc ggc                     33

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 5
tgctcgagtg cggccgttat taacaacctc cgccgctccc tccacc      46

-continued

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
ctagttattg ctcagcggtg                                          20

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 7
gggcagagtg gtccggaccg tccaaaatga tcgcc                         35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 8
ggcgatcatt ttggacggtc cggaccactc tgccc                         35

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 9
taatacgact cactataggg                                          20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 10
ccggtggccg cacgtttcag gatttc                                   26

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 11
ggccgcactc gagcaccac                                           19

<210> SEQ ID NO 12
<211> LENGTH: 39
<212> TYPE: DNA
<213> ORGANISM: Artificial Sequence
<220> FEATURE:

-continued

<223> OTHER INFORMATION: Description of Artificial Sequence:primer

<400> SEQUENCE: 12
accgccgctg cctccaccac aacctccgcc gctccctcc                              39

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 13
acgtgcggcc accggtccac ctggagggag cggcgga                               37

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 14
ggaggcagcg gcggtggatc gatggtgagc aagggcgagg                            40

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 15
ggtggtggtg ctcgagcttg                                                  20

<210> SEQ ID NO 16
<211> LENGTH: 815
<212> TYPE: DNA
<213> ORGANISM: Artificial Sequence
<220> FEATURE:
<221> NAME/KEY: CDS
<222> LOCATION: (72)..(788)
<220> FEATURE:
<223> OTHER INFORMATION: DNA encoding fusion protein

<400> SEQUENCE: 16
tgaaacgtgc ggccaccggt ccacctggag ggagcggcgg aggttgtggt ggaggcagcg      60
gcggtggatc g atg gtg agc aag ggc gag gag ctg ttc acc ggg gtg gtg     110
            Met Val Ser Lys Gly Glu Glu Leu Phe Thr Gly Val Val
              1               5                  10 ccc atc ctg gtc gag ctg gac ggc gac gta aac ggc cac aag ttc agc      158
Pro Ile Leu Val Glu Leu Asp Gly Asp Val Asn Gly His Lys Phe Ser
     15                  20                  25 gtg tcc ggc gag ggc gag ggc gat gcc acc tac ggc aag ctg acc ctg      206
Val Ser Gly Glu Gly Glu Gly Asp Ala Thr Tyr Gly Lys Leu Thr Leu
 30                  35                  40                  45 aag ttc atc tgc acc acc ggc aag ctg ccc gtg ccc tgg ccc acc ctc      254
Lys Phe Ile Cys Thr Thr Gly Lys Leu Pro Val Pro Trp Pro Thr Leu
                 50                  55                  60 gtg acc acc ctg acc tac ggc gtg cag tgc ttc agc cgc tac ccc gac      302
Val Thr Thr Leu Thr Tyr Gly Val Gln Cys Phe Ser Arg Tyr Pro Asp
             65                  70                  75 cac atg aag cag cac gac ttc ttc aag tcc gcc atg ccc gaa ggc tac      350
His Met Lys Gln His Asp Phe Phe Lys Ser Ala Met Pro Glu Gly Tyr

```
                80                  85                  90
gtc cag gag cgc acc atc ttc ttc aag gac gac ggc aac tac aag acc    398
Val Gln Glu Arg Thr Ile Phe Phe Lys Asp Asp Gly Asn Tyr Lys Thr
     95                 100                 105 cgc gcc gag gtg aag ttc gag ggc gac acc ctg gtg aac cgc atc gag    446
Arg Ala Glu Val Lys Phe Glu Gly Asp Thr Leu Val Asn Arg Ile Glu
110                 115                 120                 125 ctg aag ggc atc gac ttc aag gag gac ggc aac atc ctg ggg cac aag    494
Leu Lys Gly Ile Asp Phe Lys Glu Asp Gly Asn Ile Leu Gly His Lys
                130                 135                 140 ctg gag tac aac tac aac agc cac aac gtc tat atc atg gcc gac aag    542
Leu Glu Tyr Asn Tyr Asn Ser His Asn Val Tyr Ile Met Ala Asp Lys
            145                 150                 155 cag aag aac ggc atc aag gtg aac ttc aag atc cgc cac aac atc gag    590
Gln Lys Asn Gly Ile Lys Val Asn Phe Lys Ile Arg His Asn Ile Glu
        160                 165                 170 gac ggc agc gtg cag ctc gcc gac cac tac cag cag aac acc ccc atc    638
Asp Gly Ser Val Gln Leu Ala Asp His Tyr Gln Gln Asn Thr Pro Ile
    175                 180                 185 ggc gac ggc ccc gtg ctg ctg ccc gac aac cac tac ctg agc acc cag    686
Gly Asp Gly Pro Val Leu Leu Pro Asp Asn His Tyr Leu Ser Thr Gln
190                 195                 200                 205 tcc gcc ctg agc aaa gac ccc aac gag aag cgc gat cac atg gtc ctg    734
Ser Ala Leu Ser Lys Asp Pro Asn Glu Lys Arg Asp His Met Val Leu
                210                 215                 220 ctg gag ttc gtg acc gcc gcc ggg atc act ctc ggc atg gac gag ctg    782
Leu Glu Phe Val Thr Ala Ala Gly Ile Thr Leu Gly Met Asp Glu Leu
            225                 230                 235 tac aag ctcgagcacc accaccacca ccactga                              815
Tyr Lys

<210> SEQ ID NO 17
<211> LENGTH: 239
<212> TYPE: PRT
<213> ORGANISM: Artificial Sequence
<220> FEATURE:
<223> OTHER INFORMATION: fusion protein

<400> SEQUENCE: 17

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
```

-continued

```
            145                 150                 155                 160
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235
```

KIT FOR DETECTING ANTIGEN OR MEASURING ITS AMOUNT

TECHNICAL FIELD

The present invention relates to a kit for detecting antigen or measuring its amount and a method for detecting antigen or measuring its amount. According to the kit and the method of the present invention, an antigen can be detected or measured for its amount with high sensitivity without requiring an immobilization step and a washing step.

BACKGROUND ART

At present, immunoassays have become an increasingly important measurement technique in clinical diagnostics. In adoption of individual immunoassays, not only the enhancement of sensitivity and specificity but also rapid and easy measurement have become important factors. In the currently main immunoassays, the measurement principle for detecting protein biomarkers is a sandwich method, and the measurement principle for detecting low molecular weight materials is a competitive method. However, both methods are enzyme immunoassays, in which the activity of the enzyme mainly used as the label is measured after several times of reaction and washing, in many cases and have a problem of taking labor and time of several hours in the measurement. In contrast, homogeneous immunoassays in which a sample is mixed with measurement reagents for reaction and detection is performed have been developed.

The present inventors have recently succeeded in construction of Quenchbody (Q-body), an antibody that emits light upon binding of an antigen, as a rapid and highly sensitive measurement element that can be used in homogeneous immunoassays and have filed patent applications and published papers (WO 2011/061944, WO 2013/065314, R. Abe et al., J. Am. Chem. Soc., 2011, 133(43), 17386-17394). Q-body is a fluorescence modified antibody prepared by labeling one or two specific sites near the antigen binding site of an antibody with a fluorescent dye, such as TAMRA, via a short linker. The dye interacts with amino acids (mainly tryptophan) in the antibody into a quenched state. The quenching is released by addition of an antigen to emit light. However, the production of Q-body has required cloning of an antibody gene and has had a problem of taking time and cost for the construction.

In order to solve this problem, recently, the present inventors have focused on PAxPG, which is an antibody-binding protein (J. Dong et al., J. Biosci. Bioeng., 2015, 120, 504-509) and have succeeded in production of a complex, in which the quenching is released by addition of an antigen like Q-body, by preparing a fluorescence probe through binding of the protein and a fluorescent dye via a linker and mixing the probe with an antibody (Non-Patent Literature 1).

CITATION LIST

Non-Patent Literature

Non-Patent Literature 1: H. Jeong et al., Anal. Methods, 2016, 8, 7774-7779

SUMMARY OF INVENTION

Technical Problem

The complex of PAxPG and an antibody has an advantage of not requiring cloning of the antibody gene for preparing the complex unlike Q-body, while being capable of detecting an antigen like Q-body. However, the complex of PAxPG and an antibody has a problem of a low increase in the fluorescence intensity by addition of an antigen compared to that in Q-body.

It is an object of the present invention to provide a novel antigen detection method replacing for the antigen detection method using a complex of PAxPG and an antibody while maintaining the advantage of not requiring cloning of the antibody gene.

Solution to Problem

The present inventors have diligently studied to solve the above-mentioned problems and have found that a complex capable of detecting an antigen can be produced even if a fragment containing a C-terminal subdomain of protein M (R. Grover et al., Science, 2014, 343(6171), 656-661), which is an antibody-binding protein derived from *Mycoplasma*, is used instead of PAxPG.

A paper (R. Grover et al., Science, 2014, 343(6171), 656-661) relating to the above-mentioned protein M describes the C-terminal subdomain of the above-mentioned protein M (domain at residue Nos. 441 to 468) inhibits the binding between an antigen and an antibody. Accordingly, it was expected that the complex of a fragment including the C-terminal subdomain of protein M and an antibody does not bind to an antigen, and it was quite unexpected that the complex can be used in detection of an antigen.

In addition, it has been reported that when PAxPG is used as a fluorescence probe, even if 1 µM of an antigen is added to a complex of 50 nM of a fluorescence probe and 200 nM of a Fab fragment, the fluorescence intensity is increased by only about 2.3% to 5.3% (H. Jeong et al., Anal. Methods, 2016, 8, 7774-7779). In contrast, when a fragment of protein M is used as a fluorescence probe, the addition of an antigen increases the fluorescence intensity by 40% or more (FIG. 9). Accordingly, it will be possible to detect an antigen with higher sensitivity by using a protein M fragment instead of PAxPG.

The present invention has been accomplished based on the findings described above.

That is, the present invention provides the following aspects [1] to [14]:

[1] A kit for detecting antigen or measuring its amount, including a complex composed of a polypeptide including an antibody light chain variable region and a polypeptide including an antibody heavy chain variable region and a protein M fragment labeled with a fluorescent dye, wherein the protein M fragment is a fragment having a binding ability to the complex;

[2] The kit for detecting antigen or measuring its amount according to aspect [1], wherein the protein M fragment is a fragment including all or part of the C-terminal subdomain of protein M;

[3] The kit for detecting antigen or measuring its amount according to aspect [1], wherein the protein M fragment is a fragment having deletion of 50 to 100 amino acid residues at the N-terminal side and 50 to 100 amino acid residues at the C-terminal side of protein M;

[4] The kit for detecting antigen or measuring its amount according to any one of aspects [1] to [3], wherein the complex composed of a polypeptide including an antibody light chain variable region and a polypeptide including an antibody heavy chain variable region is a full-length antibody;

[5] The kit for detecting antigen or measuring its amount according to any one of aspects [1] to [4], wherein the fluorescent dye labels the C-terminal side of the protein M fragment;
[6] The kit for detecting antigen or measuring its amount according to any one of aspects [1] to [4], wherein the protein M fragment is labeled with two fluorescent dyes;
[7] The kit for detecting antigen or measuring its amount according to aspect [6], wherein the two fluorescent dyes are a rhodamine dye and GFP or a variant thereof;
[8] A method for detecting antigen or measuring its amount in a sample, comprising sequentially performing the following steps (1) to (3):
(1) bringing a sample into contact with a complex composed of a polypeptide including an antibody light chain variable region and a polypeptide including an antibody heavy chain variable region in the presence of a protein M fragment labeled with a fluorescent dye, wherein the protein M fragment is a fragment having a binding ability to the complex;
(2) measuring the fluorescence intensity of the fluorescent dye; and
(3) judging the presence of an antigen in the sample from the fluorescence intensity or calculating the antigen level in the sample from the fluorescence intensity;
[9] The method for detecting antigen or measuring its amount according to aspect [8], wherein the protein M fragment is a fragment including all or part of the C-terminal subdomain of protein M;
[10] The method for detecting antigen or measuring its amount according to aspect [8], wherein the protein M fragment is a fragment having deletion of 50 to 100 amino acid residues at the N-terminal side and 50 to 100 amino acid residues at the C-terminal side of protein M;
[11] The method for detecting antigen or measuring its amount according to any one of aspects [8] to [10], wherein the complex composed of a polypeptide including an antibody light chain variable region and a polypeptide including an antibody heavy chain variable region is a full-length antibody;
[12] The method for detecting antigen or measuring its amount according to any one of aspects [8] to [11], wherein the fluorescent dye labels the C-terminal side of the protein M fragment;
[13] The method for detecting antigen or measuring its amount according to any one of aspects [8] to [11], wherein the protein M fragment is labeled with two fluorescent dyes; and
[14] The method for detecting antigen or measuring its amount according to aspect [13], wherein the two fluorescent dyes are a rhodamine dye and GFP or a variant thereof.

The present application is based on, and claims priority from, Japanese Patent Application No. 2017-021164, the contents of which specification and/or drawings are incorporated herein by reference.

Advantageous Effects of Invention

According to the kit and the method of the present invention, an antigen can be detected or measured for its amount with high sensitivity without requiring an immobilization step and a washing step. In addition, the kit and the method also have an advantage of not requiring production of an antibody to be used for the detection or measurement by cloning an antibody gene.

BRIEF DESCRIPTION OF DRAWINGS

FIG. 1 shows the structure of a complex of Fab (left) and protein M (right). This structure is downloaded (ID: 4NZR) from PDB (Protein Data Bank) and displayed using PyMOL (Schrodinger). The C-terminus of protein M is present near the L-chain (VL) of an antigen binding site on the upper surface of the Fab.

FIG. 2 is a diagram schematically showing a principle of detecting an antigen using a fluorescence probe including protein M.

FIG. 3 is a diagram showing the structures of PMdQ (1), dPMdQ (2), PM-Q (3), and dPM-Q (4).

DESCRIPTION OF EMBODIMENTS

Figure 4:
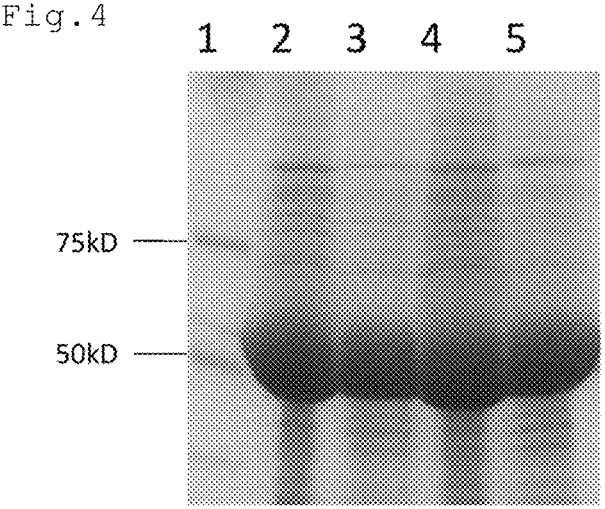
FIG. 4 is an electrophoresis photograph of a PM-Q probe. In the photograph, lanes 1, 2, 3, 4, and 5 show the results when molecular weight markers, the expression product of pET32-PM-Q, the expression product of pET32dC-PM-Q, the expression product of pET32-PMdQ, and expression product of pET32dC-PMdQ were added.

The present invention will now be described in detail.

The kit for detecting antigen or measuring its amount of the present invention includes a complex composed of a polypeptide including an antibody light chain variable region and a polypeptide including an antibody heavy chain variable region (hereinafter, this complex may be referred to as "antibody complex") and a protein M fragment labeled with a fluorescent dye.

Protein M is an antibody-binding protein derived from *Mycoplasma genitalium* (R. Grover et al., Science, 2014, 343(6171), 656-661), and the amino acid sequence thereof is as shown in SEQ ID NO: 1. Protein M consists of 556 amino acid residues and has a transmembrane domain at residues 16 to 30, a large domain at residues 78 to 440 (hereinafter, this domain may be referred to as "N-terminal subdomain"), and a small domain at residues 441 to 468 (hereinafter, this domain may be referred to as "C-terminal subdomain").

It is known that homologs of protein M are also present in bacteria of *Mycoplasma* other than *Mycoplasma genitalium* (for example, *Mycoplasma* pneumonia, *Mycoplasma iowae*, and *Mycoplasma gallisepticum*) (R. Grover et al., Science, 2014, 343(6171), 656-661). Although the term "protein M" generally refers to the protein derived from *Mycoplasma genitalium* only, in the present specification, the term "protein M" includes not only the protein derived from *Mycoplasma genitalium* but also the above-mentioned homologs.

In the present invention, protein M fragments, not protein M itself, are used. Here, the term "protein M fragment" refers to a protein having deletion of amino acid residues at the N-terminal side and/or the C-terminal side of protein M.

Although the protein M fragment may be any fragment that binds to the antibody complex, the fragment preferably includes all or part of the C-terminal subdomain of protein M. Here, the phrase "including part of the C-terminal subdomain" refers to including 50% or more, 60% or more, 70% or more, 80% or more, 85% or more, 90% or more, or 95% or more of the total amino acid residues (28 residues) of the C-terminal subdomain. In addition, the protein M fragment preferably includes all or part of the N-terminal subdomain of protein M. Here, the phrase "including part of the N-terminal subdomain" refers to including 50% or more, 60% or more, 70% or more, 80% or more, 85% or more, 90% or more, or 95% or more of the total amino acid residues (363 residues) of the N-terminal subdomain. Furthermore, the protein M fragment preferably does not include the transmembrane domain.

The protein M fragment may be a fragment having deletion, substitution, or insertion of one or several amino acids in a fragment obtained from natural protein M as long as the fragment binds to the antibody complex. Whether such an amino acid-modified fragment binds to the antibody complex or not can be examined by a generic method that is used for examining the presence or absence of the binding between proteins. For example, when a protein M fragment to be examined for binding is labeled with a fluorescent dye (e.g., TAMRA) that is used in Q-body and is brought into contact with the antibody complex, if the protein M fragment binds to the antibody complex, the fluorescence intensity decreases; and if the fragment does not bind to the antibody complex, the fluorescence intensity does not change. Accordingly, the presence or absence of binding can be examined by using the change in fluorescence intensity as an indicator.

In production of the protein M fragment, the number of amino acid residues deleted from the N-terminal side and the C-terminal side is preferably determined such that all or part of the C-terminal subdomain is included, all or part of the N-terminal subdomain is included, and the transmembrane domain is not included. Specifically, the number of residues deleted from the N-terminal side is preferably 50 to 100 and further preferably 70 to 80. The number of residues deleted from the C-terminal side is preferably 50 to 100 and further preferably 80 to 90.

The protein M fragment may be labeled with a fluorescent dye by any method. For example, it is possible to use a method in which an amino acid tag having a functional group (e.g., a thiol group or an amino group) capable of being labeled is added to a terminus of a protein M fragment via a linker and the functional group is labeled with a fluorescent dye using maleimide, succinimide, or the like. The labeling with a fluorescent dye can also use a method for site-specific labeling while synthesizing the protein M fragment using a cell-free translation system or a method for site-specific introducing of a fluorescent dye by recombinant DNA technology using an *E. coli* or animal cell as the host cell. Examples of the labeling method using a cell-free translation system include an amber suppression method (Ellman J. et al., (1991) Methods Enzymol. 202: 301-36), a four-base codon method (Hohsaka T. et al., J. Am. Chem. Soc., 118, 9778-9779, 1996), a C-terminal labeling method (Japanese Patent Laid-Open No. 2000-139468), and an N-terminal labeling method (U.S. Pat. No. 5,643,722, Olejnik et al. (2005) Methods 36: 252-260).

Although the fluorescent dye may label the N-terminal side of a protein M fragment, it is preferable to label the C-terminal side.

The fluorescent dye for fluorescence labeling may be any fluorescent dye that is quenched in a state in which a protein M fragment labeled with the fluorescent dye is binding to the antibody complex in the absence of an antigen and emits fluorescence when an antigen binds to the complex to release the quenching function. Examples of such a fluorescent dye include the fluorescent dyes used for known Q-body, such as fluorescent dyes described in the specification of International Publication No. WO 2013/065314, specifically, fluorescent dyes having rhodamine, coumarin, Cy, EvoBlue, oxazine, Carbopyronin, naphthalene, biphenyl, anthracene, phenenthrene, pyrene, carbazole, etc. as the basic structure; and derivatives of these fluorescent dyes. Specifically, examples of the fluorescent dye include CR110: carboxyrhodamine 110: Rhodamine Green (trade name), TAMRA: carboxytetramethylrhodamine: TMR, carboxyrhodamine 6G: CR6G, ATT0655 (trade name), BODIPY FL (trade name): 4,4-difluoro-5,7-dimethyl-4-bora-3a,4a-diaza-s-indancene-3-propionic acid, BODIPY 493/503 (trade name): 4,4-difluoro-1,3,5,7-tetramethyl-4-bora-3a,4a-diaza-s-indancene-8-propionic acid, BODIPY R6G (trade name): 4,4-difluoro-5-(4-phenyl-1,3-butadienyl)-4-bora-3a,4a-diaza-s-indancene-3-propionic acid, BODIPY 558/568 (trade name): 4,4-difluoro-5-(2-thienyl)-4-bora-3a,4a-diaza-s-indancene-3-propionic acid, BODIPY 564/570 (trade name): 4,4-difluoro-5-styryl-4-bora-3a,4a-diaza-s-indancene-3-propionic acid, BODIPY 576/589 (trade name): 4,4-difluoro-5-(2-pyrrolyl)-4-bora-3a,4a-diaza-s-indancene-3-propionic acid, BODIPY 581/591 (trade name): 4,4-difluoro-5-(4-phenyl-1,3-butadienyl)-4-bora-3a,4a-diaza-s-indancene-3-propionic acid, Cy3 (trade name), Cy3B (trade name), Cy3.5 (trade name), Cy5 (trade name), Cy5.5 (trade name), EvoBlue10 (trade name), EvoBlue30 (trade name), MR121, ATTO 390 (trade name), ATTO 425 (trade name), ATTO 465 (trade name), ATT0488 (trade name), ATTO 495 (trade name), ATTO 520 (trade name), ATTO 532 (trade name), ATTO Rho6G (trade name), ATTO 550 (trade name), ATTO 565 (trade name), ATTO Rho3B (trade name), ATTO Rho11 (trade name), ATTO Rho12 (trade name), ATTO Thio12 (trade name), ATTO 610 (trade name), ATTO 611X (trade name), ATTO 620 (trade name), ATTO Rho14 (trade name), ATTO 633 (trade name), ATTO 647 (trade name), ATTO 647N (trade name), ATTO 655 (trade name), ATTO Oxa12 (trade name), ATTO 700 (trade name), ATTO 725 (trade name), ATTO 740 (trade name), Alexa Fluor 350 (trade name), Alexa Fluor 405 (trade name), Alexa Fluor 430 (trade name), Alexa Fluor 488 (trade name), Alexa Fluor 532 (trade name), Alexa Fluor 546 (trade name), Alexa Fluor 555 (trade name), Alexa Fluor 568 (trade name), Alexa Fluor 594 (trade name), Alexa Fluor 633 (trade name), Alexa Fluor 647 (trade name), Alexa Fluor 680 (trade name), Alexa Fluor 700 (trade name), Alexa Fluor 750 (trade name), Alexa Fluor 790 (trade name), Rhodamine Red-X (trade name), Texas Red-X (trade name), 5(6)-TAMRA-X (trade name), 5TAMRA (trade name), and SFX (trade name). Among these dyes, CR110 and TAMRA, which are rhodamine dyes, and ATTO655, which is an oxazine dye, are examples of particularly preferable fluorescent dyes.

The protein M fragment may be labeled with a single fluorescent dye or may be labeled with two fluorescent dyes. The two fluorescent dyes are preferably a donor dye serving as an energy donor for fluorescence resonance energy transfer (FRET) and an acceptor dye serving as an energy acceptor. On this occasion, the donor dye and the acceptor dye are arranged such that they interact with each other when an antibody complex binds to a protein M fragment and that the energy emitted by the donor dye transfers to the acceptor dye. An antigen can be detected based on a change in the fluorescence intensity of the donor dye and the acceptor dye by arranging the dyes in such a manner. That is, when only the antibody complex is present, the fluorescence intensity of the donor dye is decreased by the FRET, and the fluorescence intensity of the acceptor dye is increased, compared to when the protein M fragment is present alone. When the antibody complex and an antigen are present, the antigen binds to the antibody complex to change the steric structure of the antibody complex. Consequently, FRET does not occur, and the above-described change in fluorescence intensity is offset (the fluorescence intensity of the donor dye increases, and the fluorescence intensity of the acceptor dye decreases.).

The combination of a donor dye and an acceptor dye is, for example, a combination of a rhodamine dye and GFP or a GFP variant. Here, the GFP variant is, for example, EGFP, BFP, or YFP. A most preferable combination is, for example, a combination of TAMRA and EGFP. The combination of a donor dye and an acceptor dye is not limited to the above-mentioned examples. For example, the combinations described in Japanese Patent Laid-Open No. 2014-156428, i.e., combinations of BODIPY (registered trademark) FL and BODIPY (registered trademark) 558/568, BODIPY FL and BODIPY 576/586, BODIPY FL and TAMRA, BODIPY FL and Cy3, Fluorescein and BODIPY 558/568, Alexa488 and BODIPY 558/568, and BODIPY 558/568 and Cy5, can also be used.

The protein M fragment may be added with a protein having an arbitrary amino acid sequence, a peptide tag, a linker, a solubilization tag, etc. as long as the binding ability to an antibody complex, the quenching ability at the time of binding to the antibody complex, and the dequenching ability in the presence of an antigen are not inhibited. The protein M fragment may be labeled with a radioactive isotope, an enzyme, or a fluorescent dye being a different type from the above-mentioned fluorescent dyes or may be modified by, for example, phosphorylation or methylation. Here, examples of the peptide tag include a ProX tag, a FLAG tag, a His tag, a HA tag, a Ni tag, and a Cys tag. Examples of the linker include repeated sequences of $G_4S$, DDAKK, and EAAAK, e.g., $(G_4S)_{2-6}$, $(DDAKK)_{2-6}$, and $(EAAAK)_{2-6}$. Examples of the solubilization tag include thioredoxin and amyloid precursor protein-derived solubilization tag. When a Cys tag is added to a protein M fragment and thioredoxin is further added to the fragment for labeling with a fluorescent dye, since thioredoxin includes a cysteine residue, the fluorescent dye may be added to the thioredoxin. In order to avoid this, in such a case, a variant thioredoxin prepared by replacing the cysteine residue in thioredoxin with a serine residue is preferably used instead of thioredoxin.

The antibody light chain variable region may be any antibody light chain variable region that includes a specific amino acid sequence of the antibody light chain variable region encoded by the V-region and J-region exons of an antibody light chain gene, and may be further added with an arbitrary amino acid sequence at the N-terminal and/or C-terminal side of the specific amino acid sequence of the antibody light chain variable region or may have deletion, substitution, or insertion of one or more amino acids as long as the affinity between the antibody complex and an antigen is not impaired. Such affinity with an antigen can be appropriately examined by an ordinary method, such as ELISA and FACS. The specific amino acid sequence of the antibody light chain variable region is preferably an amino acid sequence of which the 35th amino acid in a Kabat numbering system is tryptophan.

The antibody heavy chain variable region may be any antibody heavy chain variable region that includes a specific amino acid sequence of the antibody heavy chain variable region encoded by the V-region, D-region, and J-region exons of an antibody heavy chain gene, and may be further added with an arbitrary amino acid sequence at the N-terminal and/or C-terminal side of the specific amino acid sequence of the antibody heavy chain variable region or may have deletion, substitution, or insertion of one or more amino acids as long as the affinity between the antibody complex and an antigen is not impaired. Such affinity with an antigen can be appropriately examined by an ordinary method, such as ELISA and FACS. The specific amino acid sequence of the antibody heavy chain variable region is preferably an amino acid sequence of which the 36th, 47th, or 103rd amino acid in a Kabat numbering system is tryptophan.

The polypeptide including an antibody light chain variable region can include an antibody light chain or an antibody light chain and a peptide consisting of an arbitrary amino acid sequence as long as an antibody light chain variable region is contained. For example, the polypeptide may include an antibody light chain variable region added with an antibody light chain constant region (CK) and/or a hinge region. Among these polypeptides, a polypeptide including an antibody light chain variable region added with CK is preferred. Such a polypeptide can be appropriately produced depending on the antigen as a detection or measurement object. Examples of the polypeptide including an antibody light chain variable region include those described in the specification of International Publication No. WO 2013/065314.

The polypeptide including an antibody heavy chain variable region can include an antibody heavy chain or an antibody heavy chain and a peptide consisting of an arbitrary amino acid sequence as long as an antibody heavy chain variable region is contained. For example, the polypeptide may include an antibody heavy chain variable region added with an antibody heavy chain constant region ($CH_1$) and/or a hinge region or a Fc region. Among these polypeptides, a polypeptide including an antibody heavy chain variable region added with $CH_1$ is preferred. Such a polypeptide can be appropriately produced depending on the antigen as a detection or measurement object. Examples of the polypeptide including an antibody heavy chain variable region include those described in the specification of International Publication No. WO 2013/065314.

The complex (antibody complex) composed of a polypeptide including an antibody light chain variable region and a polypeptide including an antibody heavy chain variable region may be any complex including the polypeptide including an antibody light chain variable region and the polypeptide including an antibody heavy chain variable region as components and being in a complex form and may further include, in addition to the above-mentioned polypeptides, a peptide, a protein, a lipid, a metal, or any other compound as components as long as the affinity with an antigen is not impaired.

In addition, the antibody complex is a structure substance in which the polypeptides are combined to each other and function as one component, and the presence or absence of a chemical bond between the polypeptides is not particularly considered. Examples of the bond include a disulfide bond between the polypeptides and a bond formed using a cross-linking agent. These bonds may be used in combination for one complex. Among these bonds, a disulfide bond is suitable. The antibody complex is preferably formed such that the distance between the polypeptides is short and is preferably a complex including a peptide having such a function and consisting of a polypeptide including an antibody light chain variable region and a polypeptide including an antibody heavy chain variable region. In the antibody molecule, the antibody light chain constant region and the antibody heavy chain constant region interact with each other to shorten the distance between the antibody light chain variable region and the antibody heavy chain variable region and thereby plays a peripheral role in formation of a strong antigen-binding pocket. Accordingly, the antibody complex is preferably a Fab antibody which is one antibody protein molecule in which a polypeptide consisting of an antibody light chain variable region and an antibody light chain constant region and a polypeptide chain consisting of an antibody heavy chain variable region and an antibody heavy chain constant region are bonded to each other by a disulfide bond, a $F(ab')_2$ antibody in which two Fab antibodies are bonded by a disulfide bond via a hinge, or a full-length antibody including the Fc region too. In the method using PAxPG as a fluorescence probe (H. Jeong et al., Anal. Methods, 2016, 8, 7774-7779), since PAxPG binds to not only the Fab region but also the Fc region, a full-length antibody cannot be used. Therefore, the capability of using a full-length antibody is one of major characteristics of the present invention.

Although the antibody complex may be prepared by recombinant DNA technology (for example, may be prepared in accordance with the method described in the specification of International Publication No. WO 2013/065314) as in the conventional Q-body, in the present invention, a commercially available antibody or a commercially available antibody treated with an enzyme (e.g., papain or pepsin), such as a Fab antibody or a $F(ab')_2$ antibody, can be directly used. Accordingly, it is preferred to use these antibodies from the viewpoint of ease of production.

The antigen may be any antigen that is specifically recognized by the polypeptide including an antibody light chain variable region, the polypeptide including an antibody heavy chain variable region, or the antibody complex, and examples thereof include proteins, peptides, carbohydrates, lipids, glycolipids, low molecular weight compounds, and modified proteins due to protein modifications such as phosphorylation and methylation. The kit for detecting antigen or measuring its amount of the present invention is excellent in detection sensitivity and is therefore useful especially for detection of low molecular weight compounds.

The kit for detecting antigen or measuring its amount of the present invention may include other components in addition to an antibody complex and a protein M fragment labeled with a fluorescent dye. Examples of such other components include an antigen used as a reference material, reagents usually used in such immunoassay kits, tools, and an instruction manual.

The method for detecting antigen or measuring its amount of the present invention is a method for detecting antigen or measuring its amount in a sample and is characterized by sequentially performing (1) a step of bringing a sample into contact with a complex (antibody complex) composed of a polypeptide including an antibody light chain variable region and a polypeptide including an antibody heavy chain variable region in the presence of a protein M fragment labeled with a fluorescent dye, (2) a step of measuring the fluorescence intensity of the fluorescent dye, and (3) a step of judging the presence of an antigen in the sample from the fluorescence intensity or calculating the antigen level in the sample from the fluorescence intensity. This method for detecting antigen or measuring its amount can be performed using the above-described kit for detecting antigen or measuring its amount of the present invention.

In the present invention, the "detection of an antigen" means the judgement whether an antigen is present or not in a sample, and "measurement of an antigen" means the determination of the amount of an antigen present in a sample.

The sample may be any sample having a possibility of containing an antigen as the detection or measurement object and may be a liquid sample or a sample other than liquid.

A liquid sample may be directly used as a detection or measurement object or may be diluted with, for example, a buffer solution or a saline solution or concentrated or appropriately adjusted in, for example, the pH or the salt concentration and then may be used as a detection or measurement object as long as the antigen is not damaged or the detection or measurement is not inhibited. Examples of the liquid sample include body fluids such as serum, plasma, saliva, spinal fluid, and urine, culture supernatants, cell extracts, bacterial extracts, and industrial wastewater.

The sample other than liquid, such as a solid, is preferably dissolved, suspended, or immersed in a liquid, such as a buffer solution or a saline solution, into a state of capable of being in contact with the antibody complex and is then used as a sample. In addition, the sample may be subjected to treatment, such as fractionation, shredding, pulverization, grinding, or sectioning, before being dissolved, suspended, or immersed in a liquid, or may be subjected to treatment for removing or extracting a specific component.

In the present invention, a body fluid, such as blood or spinal fluid, and a tissue in a living body can also be used as a sample for detection or measurement. That is, it is possible to bring an antibody complex into contact with an antigen in vivo by administering the antibody complex and a protein M fragment labeled with a fluorescent dye to a nonhuman animal, such as an experimental animal. The nonhuman animal used here may be any animal other than human beings, and examples thereof include vertebrates, in particular, such as mammals, fish, birds, reptiles, and amphibians. Among these animals, mammals are preferred, and mice, rats, hamsters, monkeys, and pigs are more preferred. In addition, the administration method is not particularly limited and can be appropriately selected from local parenteral administration methods, such as intramuscular injection, intraperitoneal injection, intravenous injection, subcutaneous injection, implantation, and application, and oral administration methods. Furthermore, other agents may be administered simultaneously with or before or after the administration of the antibody complex and the protein M fragment labeled with a fluorescent dye. It is also possible to observe the position or the movement of an antigen or the antigen level or changes thereof in vivo by administering an antibody complex and a protein M fragment labeled with a fluorescent dye to a nonhuman animal. In such observation, it is also possible to measure the fluorescence intensity or observe the localization of fluorescence by collecting the body fluid and tissues over time, or it is also possible to detect and observe the fluorescence intensity or changes thereof or the localization of fluorescence or the movement thereof in vivo in real time.

The contact of the sample with the antibody complex may be performed under any conditions and is usually performed in a liquid phase. The reaction conditions for the contact can be the same as those for conventional Q-body and can be those described in the specification of International Publication No. WO 2013/065314. Specifically, the temperature conditions are, for example, 1° C. to 30° C., preferably 18° C. to 25° C.; and the reaction time is, for example, from a moment up to 180 minutes, preferably 1 to 90 minutes. When the reaction is performed in a nonhuman animal body, after administration, for example, incubation is performed for 5 to 180 minutes, preferably 60 to 120 minutes, and according to need, treatment such as extraction of tissues, blood, cells, or the like or exposure of an observation object portion can be appropriately performed.

When an antigen as the detection or measurement object is present in a sample, the antibody complex recognizes the antigen. On this occasion, the quenching of the fluorescent dye of the protein M fragment binding to the antibody complex is released to emit fluorescence by irradiation of excitation light. In contrast, when the antigen as the detection or measurement object is not present in a sample, the quenching of the fluorescent dye of the protein M fragment binding to the antibody complex is maintained, fluorescence is not emitted even if excitation light is irradiated. Thus, the present invention can perform direct detection or measurement without performing a step such as washing, which is one of major characteristics of the present invention.

The fluorescence intensity may be measured by any method that can measure the fluorescence intensity emitted from a fluorescent dye, and the fluorescence intensity of the fluorescent dye may be measured by irradiating the sample after contact reaction with excitation light. The wavelengths of the excitation light for irradiation and the fluorescence to be measured can be appropriately selected according to the type of the fluorescent dye used. For example, when CR110 is used as the fluorescent dye, a combination of an excitation light wavelength of 480 nm and a fluorescence wavelength of 530 nm can be used. When TAMRA is used, a combination of an excitation light wavelength of 530 nm and a fluorescence wavelength of 580 nm can be used. When ATTO655 is used, a combination of an excitation light wavelength of 630 nm and a fluorescence wavelength of 680 nm can be used.

The light source and the measurement apparatus used for fluorescence intensity measurement can be appropriately selected. Any light source that can perform irradiation with an excitation light wavelength can be used, and examples thereof include a mercury lamp, a xenon lamp, an LED, and laser light source, and excitation light with a specific wavelength can be obtained by using an appropriate filter. As the fluorescence measuring apparatus, a device that is usually used for fluorescence observation can be used, and a microscope equipped with an excitation light source and its irradiation system and a fluorescent image acquisition system, such as MF20/FluoroPoint-Light (manufactured by Olympus Corporation) and FMBIO-III (manufactured by Hitachi Software Engineering Co., Ltd.), can be appropriately used. Since the fluorescence intensity and the antigen concentration are in positive correlation, a standard curve showing a relationship between antigen concentration and fluorescence intensity is formed by measuring fluorescence intensities of samples of which the antigen concentrations are known, and an unknown antigen concentration can be calculated from this standard curve. As such calculation of antigen concentration, the antigen level can also be automatically calculated by, for example, a conversion equation set based on a standard curve formed in advance. The fluorescence intensity measurement may be measurement of fluorescent spectrum or measurement of fluorescence intensity at a specific wavelength.

When the antibody complex and the protein M fragment labeled with a fluorescent dye are administered to a nonhuman animal, the fluorescence intensity of the fluorescent dye can also be two-dimensionally or three-dimensionally measured by irradiating the detection object region of the nonhuman animal with excitation light, instead of collection of the body fluid or tissues. In such a case, for example, a fluorescence microscope, a fluorescence image analyzer, or an endoscope equipped with a light source is used. On the detection, it is preferable to also acquire images showing the structure of the nonhuman animal individual, tissues, or cells using an endoscope, X-ray, CT, MRI, ultrasonic waves, or a microscope. Since the measured fluorescence intensity and the antigen level are in positive correlation, the localization (position) and/or the level of the antigen can be determined based on the two-dimensional or three-dimensional image of the measured fluorescence. On this occasion, comparison with the above-mentioned image showing the structure is also possible. In these measurements of fluorescence intensity, it is preferable to prepare a combination of samples excluding the antibody complex and the protein M fragment labeled with a fluorescent dye, a buffer solution used for dilution of a sample, etc. for measurement of a negative control and to measure the fluorescence intensity simultaneously. The antigen level can also be calculated using a fluorescence intensity ratio obtained by dividing the measured value of an objective sample by the measured value of the negative control. Alternatively, since the fluorescence intensity and the antigen level are in positive correlation, the presence of the antigen in a measurement sample can also be judged when the fluorescence intensity exceeds an appropriately set threshold.

As described above, according to the present invention, all antigens that can be measured by immunoassay, such as ELISA, immunodiffusion, latex agglutination, immunochromatography, and surface plasmon resonance, can be detected or measured for its amount. For example, although immunoassay of low molecular weight materials is usually competitive ELISA, the detection or measurement of a low molecular weight material by the present invention is superior to competitive ELISA in, for example, the simplicity of the method, measurement sensitivity, and SN ratio, and the ability can be exhibited mostly. Examples of the low molecular weight compound suitable for such detection or measurement of the present invention include stimulant and narcotic drugs, such as amphetamine, methamphetamine, morphine, heroin, and codeine; fungal toxins, such as aflatoxin, sterigmatocystin, neosolaniol, nivalenol, fumonisin, ochratoxin, and an endophyte producing toxin; sex hormones, such as testosterone and estradiol; additives illegally used for feed, such as clenbuterol and ractopamine; toxic substances, such as PCB, gossypol, histamine, benzpyrene, melamine, acrylamide, and dioxin; pesticide residues, such as acetamiprid, imidacloprid, chlorfenapyr, malathion, carbaryl, clothianidin, triflumizole, chlorothalonil, spinosad, Lannate, methamidophos, and chlorpyrifos; and environmental hormones, such as bisphenol A.

In addition, according to the present invention, the measurement results can be obtained instantly, and also the device can be reduced in size and cost due to the simplicity of the detection or measurement method. These advantages are not limited in low molecular weight materials and can also be exhibited in on-site analysis to go to the site and perform measurement. In addition, the measurement is easy and therefore can be performed even by a non-expert. The ability can be thoroughly exhibited in, for example, clinical diagnostic field including POCT for influenza, cause viruses and bacteria of communicable diseases, infectious diseases, and so on, and drug blood levels; simple health measurement field at work, school, nursery school, and home; safety and security field such as measures for terrorism by anthrax, botulinum toxin, sarin, VX gas, etc.; environmental field such as environmental pollutants and house dust that require on-site measurement; and research and development field requiring immunoassay.

EXAMPLES

The present invention will now be described in further detail with reference to examples but is not limited to these examples.

[Example 1] Construction of PM-Q Probe Expression Vector

In all experiments, water purified with Milli-Q (Merck Millipore) and sterilized in an autoclave was used. Hereinafter, the water is referred to as sterile water. The common reagents used were those of Sigma, Nacalai Tesque, Inc., FUJIFILM Wako Pure Chemical Corp., or Kanto Chemical Co., Ltd. unless otherwise specified.

A gene sequence (SEQ ID NO: 2) encoding the residues 78-468 of protein M (FIG. 1) was synthesized (Eurofin Genomics). In order to insert this sequence into an expression vector pET32a (Novagen), the synthesized sequence and the expression vector were each cleaved by restriction enzymes NcoI and NotI, followed by ligation, transformation, and ampicillin medium selection in accordance with ordinary methods. The resulting colony was cultured, and plasmids were extracted to select a plasmid including the inserted sequence.

Subsequently, in order to insert a tag sequence including a cysteine (Cys) residue into the C-terminus of protein M via a linker, the following procedure was performed. Incidentally, the C-terminal subdomain probably affects the antigen binding, and accordingly, protein M having deletion of the C-terminal subdomain (hereinafter referred to as PMd) was also produced. In order to insert $(SGGG)_2C$ into each of the C-termini of PMd and PM, DNA was denatured by incubation at 94° C. for 2 minutes using a pair of a primer DeltaC_SGGG2C_back(5'-GAGAACTATTATCCCTCAG-GTGGAGGGAGCGGC-3', SEQ ID NO: 3) or C-term_SGGG2C_back (5'-CTGAAACGTGCGGCCTC-AGGTGGAGGGAGCGGC-3', SEQ ID NO: 4) and SGGG2For (5'-TGCTCGAGTGCGGCCGTTATTAACAA-CCTCCGCCGCTCCCTCCACC-3', SEQ ID NO: 5) and a KOD-Plus-Neo polymerase (Toyobo Co., Ltd.). Subsequently, 30 cycles of reaction at 94° C. for 30 seconds, at 55° C. for 30 seconds, and at 68° C. for 1 minute were performed, and amplified fragments were ligated using a vector cleaved by SmaI-NotI or NotI and an In-Fusion HD cloning kit (Clontech Laboratories, Inc.; Takara Bio Inc.). The sequences of these products were verified using a T7 terminator primer (5'-CTAGTTATTGCTCAGCGGTG-3', SEQ ID NO: 6) and were defined as pET32-PMdQ and pET32-PM-Q, respectively.

[Example 2] Removal of Cys Residue from Thioredoxin in PM-Q Probe Expression Vector The pET32 was designed to express a protein in a form fused with thioredoxin at the N-terminus (hereinafter Trx) in order to improve the solubility of the protein. However, since Trx contains two Cys residues, which have a possibility of being modified by a fluorescent dye, near to each other (residues 33 and 36), these residues were substituted with serine (Ser). Mutation was performed using primers TrxMutCS2-top (5'-GGGCAGAGTGGTCCGGACCGTC-CAAAATGATCGCC-3', SEQ ID NO: 7) and TrxMutCS2-bottom (5'-GGCGATCATTTTGGACGGTCCGGAC-CACTCTGCCC-3', SEQ ID NO: 8) by a QuikChange mutagenesis kit (Stratagene, Agilent Technologies, Inc.), and the sequence was verified using a T7 promoter primer (5'-TAATACGACTCACTATAGGG-3', SEQ ID NO: 9). This procedure was performed for pET32-PMdQ and pET32-PM-Q to obtain pET32d-PMdQ and pET32d-PM-Q.

[Example 3] Expression and Purification of Fusion Protein

E. coli SHuffle T7 lysY was transformed using pET32-PMdQ, pET32-PM-Q, pET32dC-PMdQ, and pET32dC-PM-Q. Subsequently, the E. coli carrying a plasmid was cultured in 100 mL of an LBA medium (10 g/L triptone, 5 g/L yeast, 5 g/L NaCl, and 100 µg/mL ampicillin) at 30° C. until the $OD_{600}$ became 0.6, and IPTG was then added thereto to 0.4 mM, followed by incubation at 16° C. for further 16 hours. The cells were collected by centrifugation. E. coli cells suspended in 10 mL of an extraction buffer (50 mM sodium phosphate, 300 mM sodium chloride, pH 7.0) were disrupted with a cell crushing apparatus (One Shot Disruptor, Constant Systems Ltd.), followed by centrifugation at 1000×g for 20 minutes. The supernatant was collected and was purified by immobilized metal affinity chromatography. Specifically, an appropriate amount of TALON (Clontech Laboratories, Inc.; Takara Bio Inc.) agarose gel was added to the supernatant, followed by stirring for 30 minutes. Subsequently, the gel was transferred to a column and was washed with 10 mL of the extraction buffer three times, and the protein bound to the gel was eluted with 2.5 mL of an extraction buffer containing 150 mM imidazole. The results of SDS-PAGE analysis are shown in FIG. 4. A band of expected molecular weight was identified. The buffer solution was changed to PBST (PBS+0.05% Tween 20) and concentrated using Nanosep Centrifugal-3k Ultrafiltration Device (Pall Corporation), and glycerin was added thereto at a final concentration of 15%, followed by dispensation and storage at −80° C. Incidentally, the expression product of pET32-PM-Q and pET32-PMdQ containing the C-terminal subdomain was stably expressed with a high yield compared to the expression product of pET32dC-PM-Q and pET32dC-PMdQ not containing the C-terminal subdomain.

[Example 4] Labeling of Fusion Protein with Fluorescent Dye

In order to reduce Cys residues, 75 µg of the purified protein was treated with the same amount of Immobilized TCEP gel (Thermo Fisher Scientific) at room temperature for 30 minutes. The supernatant of centrifugation was collected, and 20-fold molar amount of maleimide dye was added thereto to react Cys in the protein and the dye maleimide while rotating slowly with shielding light at 4° C. for 2 hours. As dyes, 5(6)-TAMRA C6 (AAT Bioquest, Inc.), 5(6)-TAMRA C5 (Biotium), and ATTO520-C2 (ATTO-Tech) were used. After the reaction, centrifugal washing with 500 µL of PBST was performed using Nanosep ultrafiltration membrane (Pall Corporation) three times to remove unreacted dye. Furthermore, according to need, purification is further performed using a TALON or His SpinTrap column (GE Healthcare) to completely remove the dye. Finally, buffer replacement to PBST and concentration were performed using Nanosep ultrafiltration membrane, and glycerin was added thereto at a final concentration of 15%, followed by dispensation and storage at −25° C. The concentrations of these fluorescence-labeled proteins were determined by exciting the protein and TAMRA dye having a known concentration with a fluorescence spectrophotometer (JASCO Corporation, FP-8500) at 545 nm, measuring their fluorescence intensities at a peak wavelength near 580 nm and comparing the fluorescence intensities.

[Example 5] Fluorescence Measurement

Figure 5:
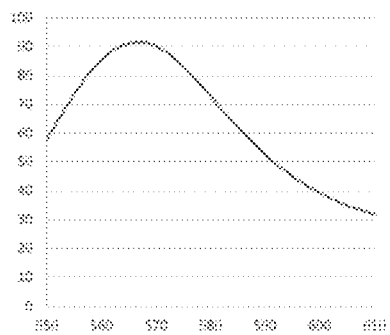
FIG. 5 includes graphs showing the results of measurement of fluorescence intensity of PMdQ (upper left), PM-Q (upper right), dPMdQ (lower left), and dPM-Q (lower right).
Figure 5:
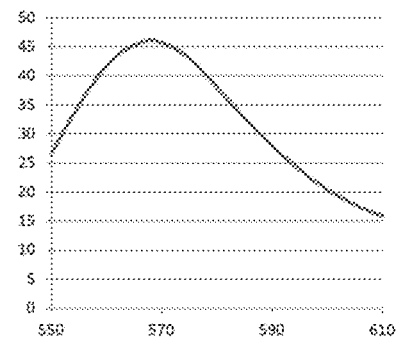
Figure 5:
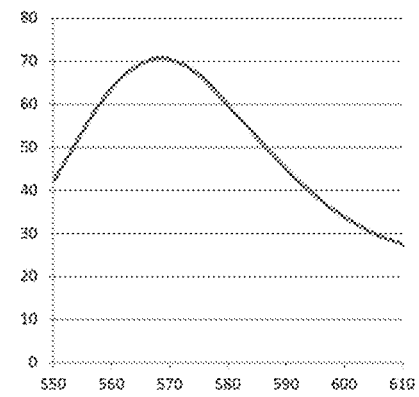
Figure 5:
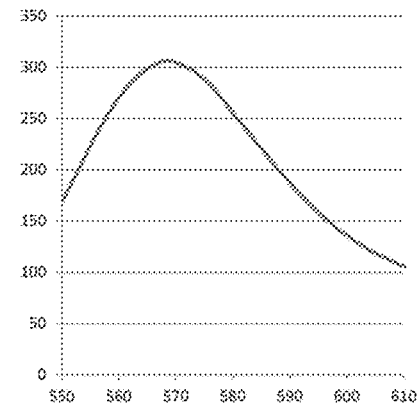
Figure 6:
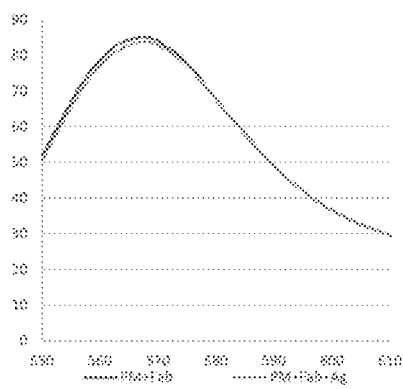
FIG. 6 includes graphs showing the results of measurement of fluorescence intensity of PMdQ (upper left), PM-Q (upper right), dPMdQ (lower left), and dPM-Q (lower right) in the presence of an anti-BGP Fab fragment and in the presence of an anti-BGP Fab fragment and an antigen.
Figure 6:
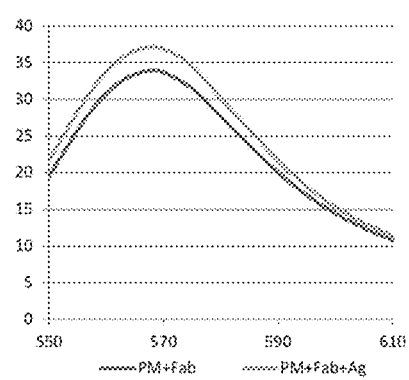
Figure 6:
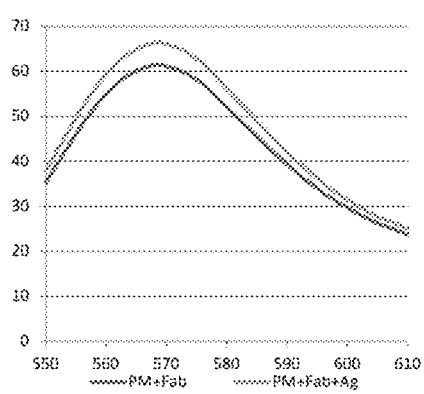
Figure 6:
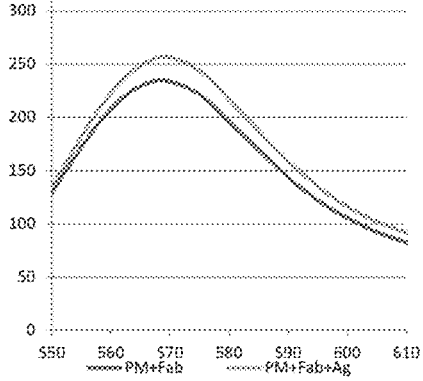

The thus-obtained fluorescence-labeled probes (hereinafter referred to as PMdQ, PM-Q, dPMdQ, and dPM-Q) were diluted with 250 µL of PBST and were excited with a fluorescence spectrophotometer at near 540 nm, and the fluorescence intensities were measured at near 580 nm (FIG. 5). Thirty minutes after the start of measurement, an anti-BGP Fab fragment (2 to 10 µL) was added thereto at a final concentration of 10 nM. As a result, a decrease in the fluorescence intensity was observed over several minutes. In contrast, when PBST was added instead of the Fab, no significant decrease was observed. After the addition of the anti-BGP Fab fragment, an antigen (BGP-C7) was further added thereto. As a result, an increase in the fluorescence intensity was observed excluding the case using PMdQ. FIG. 6 shows the results of measurement of fluorescence intensities in the presence of the anti-BGP Fab fragment and in the presence of the anti-BGP Fab fragment and an antigen.

Figure 7:
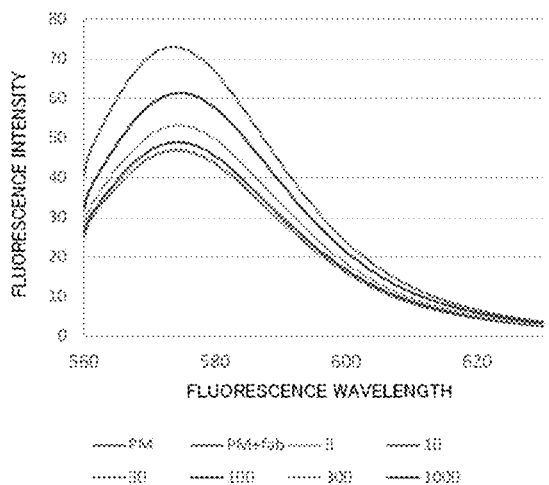
FIG. 7 includes graphs showing the results of measurement of fluorescence intensity when various concentrations of an antigen solution or PBST were added to a fluorescence-labeled probe.
Figure 7:
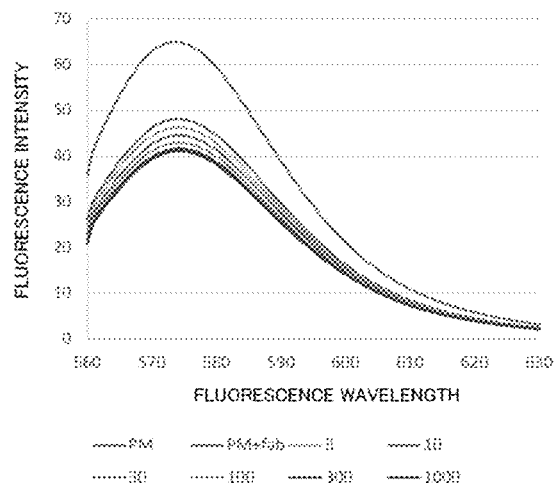
Figure 8:
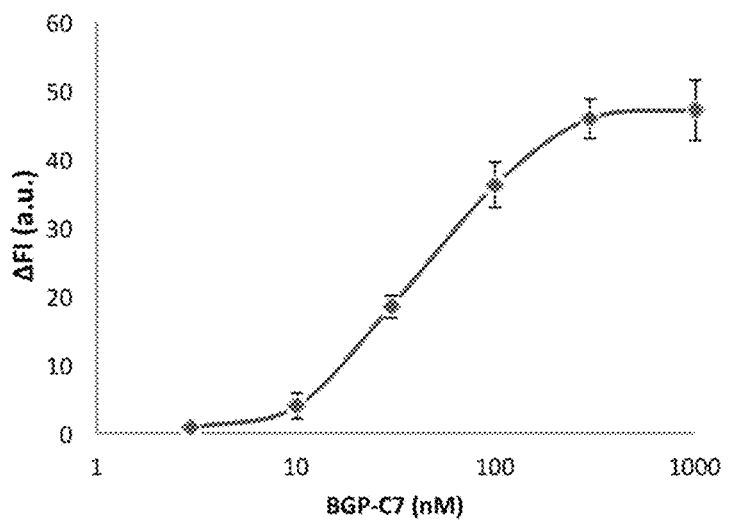
FIG. 8 is a graph showing antigen concentration-dependent changes in fluorescence intensity by addition of an antigen.
Figure 9:
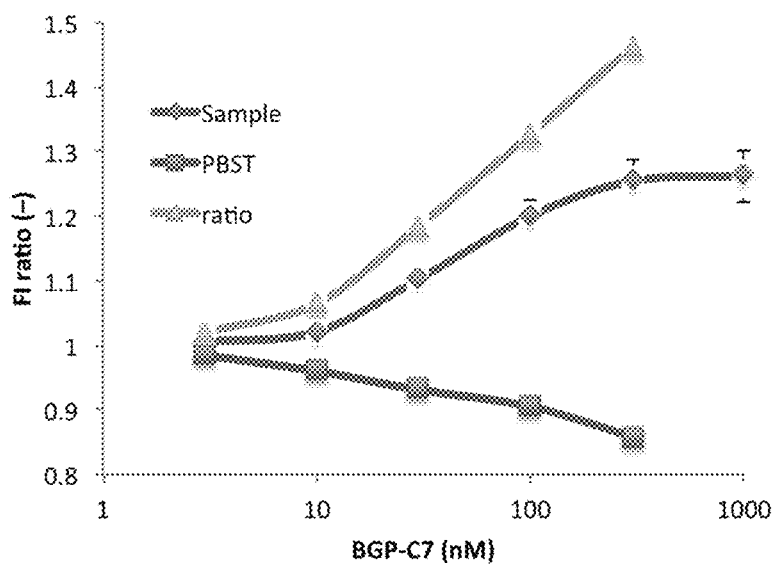
FIG. 9 is a graph normalized by the presence or absence of antigen addition. In the graph, Sample represents the measured values shown in FIG. 8, PBST represents the measured values when a buffer solution in an amount equal to the amount of the antigen was added, and ratio represents the ratios of Sample/PBST.

Subsequently, samples were prepared by adding an anti-BGP Fab fragment to dPM-Q, and 10 µL of an antigen solution was further added to the sample at antigen concentrations of 3, 10, 30, 100, 300, and 1000 nM or 10 µL of PBST was stepwise added to the sample, and changes in the fluorescence intensity were measured (FIG. 7). Furthermore, the fluorescence intensities were normalized by the fluorescence intensity at the time of addition of the antigen and were expressed by a ratio of that at the presence of antigen addition to that at the absence of antigen addition (FIG. 9). As a result, it was demonstrated that the fluorescence intensity was increased by the addition of an antigen to a mixture (complex) of a labeled probe and Fab. That is, it was revealed that the labeled probe binds to Fab and can show the properties as Q-body.

Incidentally, as the anti-BGP Fab, a fragment including $V_H/V_L$ derived from KTM-219 not having a tag sequence for modification at the N-terminus and including CH1/Ck derived from human IgG1 (Dong et al., J. Biosci. Bioeng. 122, 125-130, 2016) was prepared by the method described in the paper.

[Example 6] Detection of Antigen Using Full-Length Antibody

Figure 10:
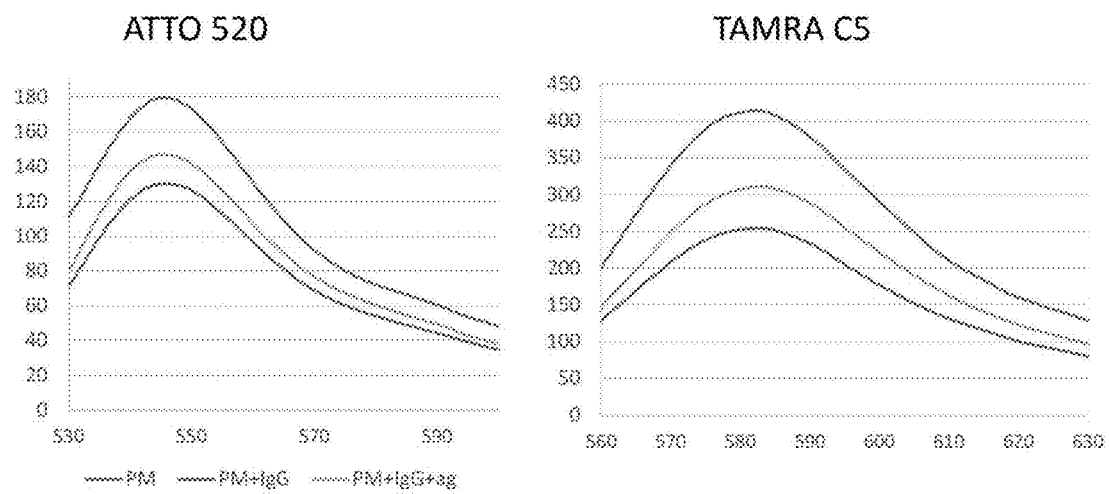
FIG. 10 includes graphs showing the results of measurement of fluorescence intensity of fluorescence probes labeled with ATTO520-C2 (graph on the left) or TAMRA C5 (graph on the right).

Anti-osteocalcin full-length antibody (KTM219 IgG, 5 nM) was added to 10 nM fluorescence-labeled probe (dPM-Q labeled with ATTO520-C2 or TAMRA C5), and 1 µM antigen (BGP-C7) was further added thereto. The fluorescence intensity was measured by irradiation of excitation light before the antibody addition, after the antibody addition, and after the antigen addition. The results are shown in FIG. 10.

In both cases of using ATTO520-C2 or TAMRA C5 as the fluorescent dye, the fluorescence intensity was decreased by addition of the antibody (ATTO520-C2: a decrease of 27%, TAMRA C5: a decrease of 38%), and the fluorescence intensity was increased by addition of the antigen (ATTO520-C2: an increase of 10%, TAMRA C5: an increase of 13%). These results revealed that the fluorescence-labeled probe of the present invention can form a complex with not only an antibody fragment but also a full-length antibody, and the complex can detect an antigen.

[Example 7] Measurement of Full-Length Human BGP

Figure 11:
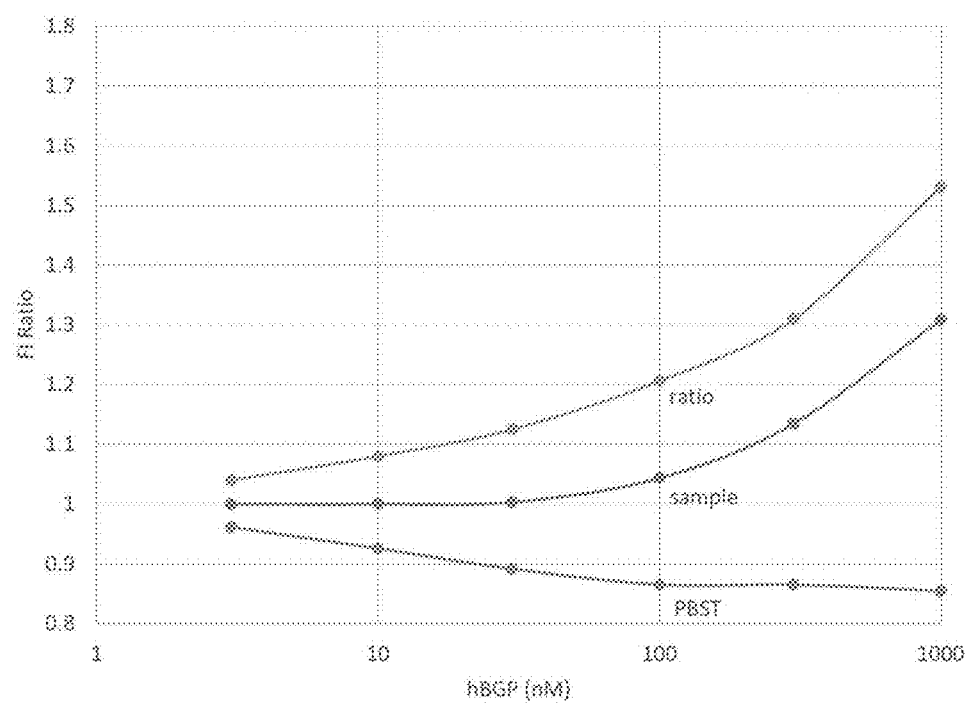
FIG. 11 is a graph showing full-length human BGP concentration-dependent changes in fluorescence intensity (fluorescent dye: TAMRA C5). In the graph, sample represents the measured values of an antigen solution, PBST represents the measured values when a buffer solution in an amount equal to the amount of the antigen was added, and ratio represents the ratios of sample/PBST.
Figure 12:
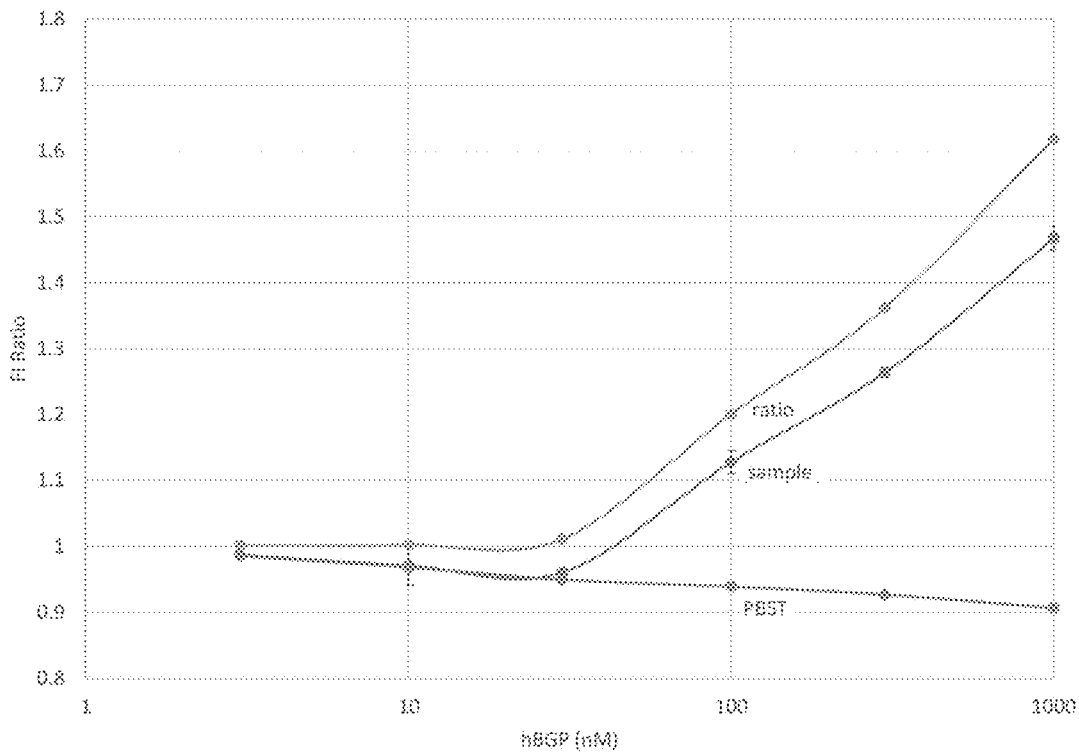
FIG. 12 is a graph showing full-length human BGP concentration-dependent changes in fluorescence intensity (fluorescent dye: TAMRA C6). In the graph, sample represents the measured values of an antigen solution, PBST represents the measured values when a buffer solution in an amount equal to the amount of the antigen was added, and ratio represents the ratios of sample/PBST.

An anti-BGP Fab fragment (5 nM) was added to 5 nM fluorescence-labeled probe (dPM-Q labeled with TAMRA C5 or TAMRA C6), and various concentrations of full-length (49 amino acids) human BGP as an antigen was added thereto to measure changes in the fluorescence intensity. The concentrations of the full-length human BGP as the antigen were 3, 10, 30, 100, 300, and 1000 nM, and the volume thereof was 10 μL. The same amount of PBST was added instead of the antigen solution, and changes in the fluorescence intensity were similarly measured. The results are shown in FIGS. 11 and 12.

As shown in these figures, the fluorescence intensity increased depending on the concentration of the full-length human BGP. This result revealed that not only the BGP-C7 consisting of seven amino acids but also full-length human BGP having a large molecular weight (about 6 kDa) can be measured by the labeled probe. In addition, it is suggested that the full-length human BGP can be measured with better response and higher sensitivity when labeled with TAMRA C6 (FIG. 12) compared to when labeled with TAMRA C5 (FIG. 11).

[Example 8] Construction of pET32-PMEGFP

I Experimental Method
1.1 Experimental Material
The sterile water used in this example was all water (Milli-Q water) purified with a Milli-Q water production device (Merck Millipore) and then sterilized in an autoclave. The oligonucleotides used were synthesized by Eurofins Genomics K.K. according to our request. The restriction enzymes were purchased from New England Biolabs Japan Inc. or Takara Bio Inc.
1.1.1 Oligonucleotide
The nucleotide sequences of the used oligonucleotides were as follows:

PM_AgeFor:
(SEQ ID NO: 10)
5'-CCGGTGGCCGCACGTTTCAGGATTTC-3', pET_EagBack:
(SEQ ID NO: 11)
5'-GGCCGCACTCGAGCACCAC-3', GSCGS_For:
(SEQ ID NO: 12)
5'-ACCGCCGCTGCCTCCACCACAACCTCCGCCGCTCCCTCC-3', -continued Age_P2GSCGS_Back:
(SEQ ID NO: 13)
5'-ACGTGCGGCCACCGGTCCACCTGGAGGGAGCGGCGGA-3', EGFP_Back:
(SEQ ID NO: 14)
5'-GGAGGCAGCGGCGGTGGATCGATGGTGAGCAAGGGCGAGG-3',
and EGFP_XhoI_For:
(SEQ ID NO: 15)
5'-GGTGGTGGTGCTCGAGCTTG-3'.

1.1.2 *Escherichia coli*
The used *E. coli* cells are as follows:
XL10-Gold (Kan$^r$): Tet$^r$, Δ(mcrA)183, Δ(mcrCB-hsdSMR-mrr)173, endA1, supE44, thi-1, recA1, gyrA96, relA1, lac, Hte, and [F', proAB, lacI $^q$ZΔM15, Tn10 (Tet$^r$), Tn5 (Kan$^r$), Amy].

Figure 13:
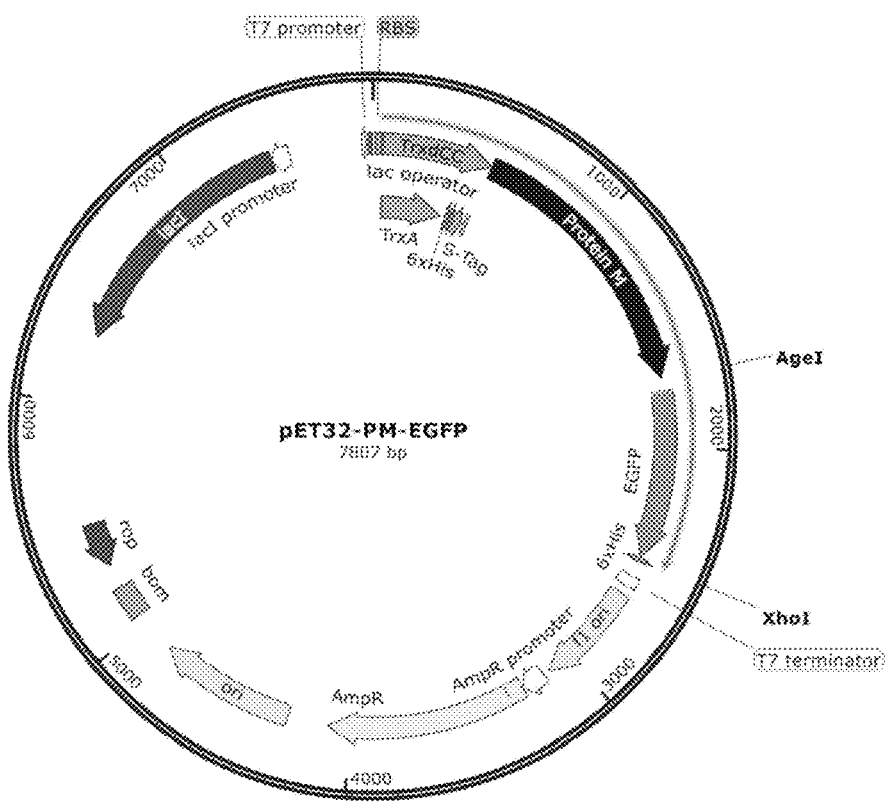
FIG. 13 is a diagram showing the structure of pET32-PMEGFP.
Figure 14:
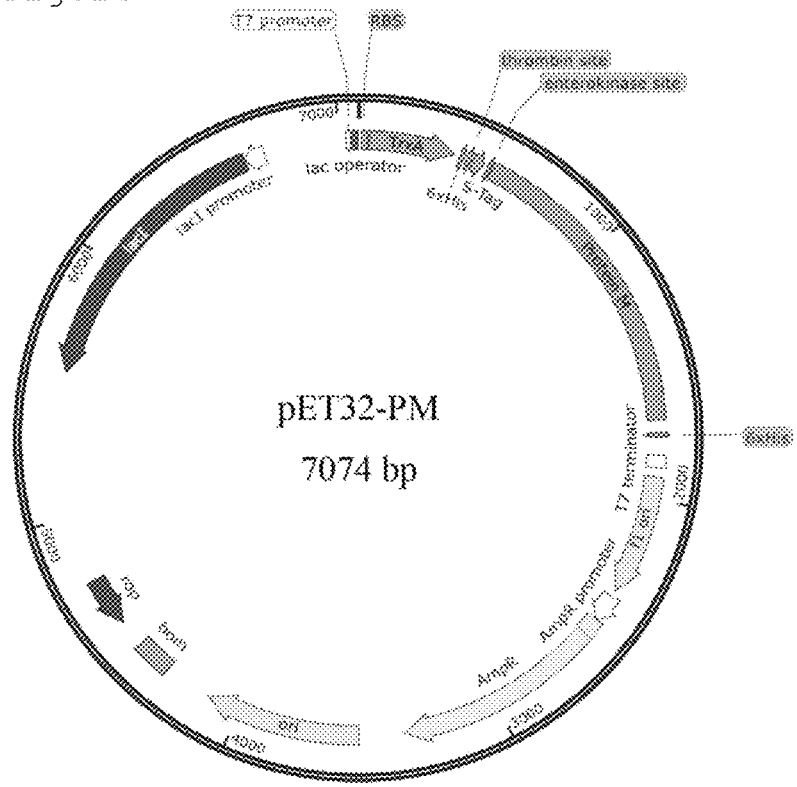
FIG. 14 is a diagram showing the structure of pET32-PM.
Figure 15:
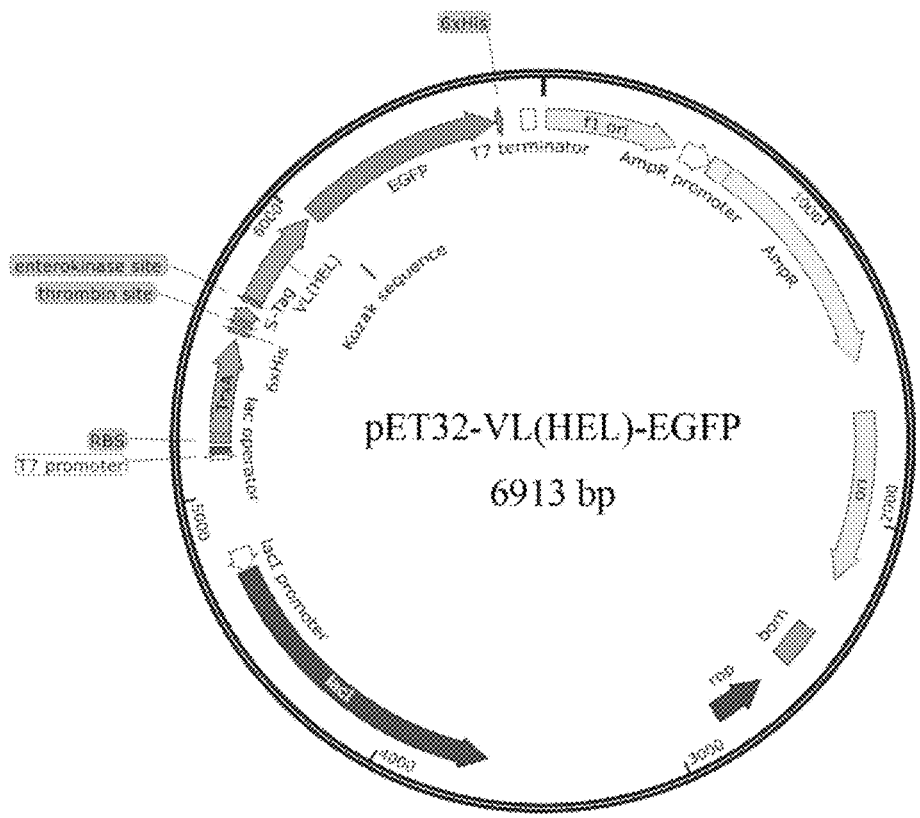
FIG. 15 is a diagram showing the structure of pET32-VL (HEL)-EGFP.

*E. coli* was cultured in an LB medium sterilized in an autoclave and containing an antibiotic. The antibiotic was prepared to be 100 μg/mL ampicillin (Amp) or 50 μg/mL kanamycin (Km).
1.2 Construction of pET32-PMEGFP
In construction of pET32-PMEGFP (FIG. 13), a plasmid pET32-PM (FIG. 14) constructed by Mr. Chihiro MIYAKE was used as a vector. Amplification using pET32-PM as a template was performed by PCR using primers PM_AgeFor and pET_EagBack, followed by purification. As two inserts, EGFP and a linker were prepared. The former was amplified by PCR using pET32-VL(HEL)-EGFP (FIG. 15) as a template and using primers EGFP Back and EGFP_XhoI_For and were purified. In the latter, since the number of the nucleotides was small, amplification by PCR was performed without using a template and using primers GSCGS_For and Age_P2GSCGS_Back, and purification was performed.

Figure 16:
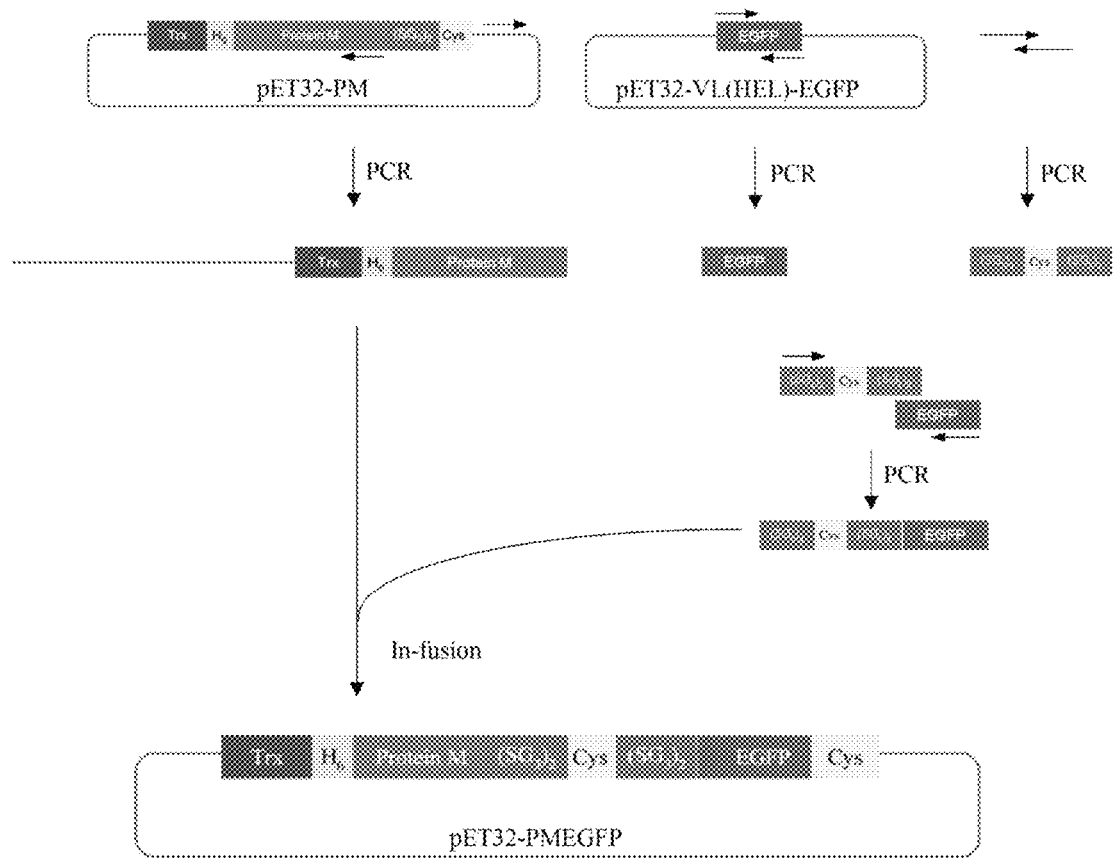
FIG. 16 is a diagram schematically showing a method for constructing pET32-PMEGFP.
Figure 17:
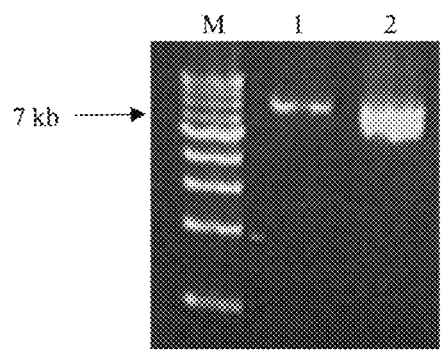
FIG. 17 shows the result of electrophoresis after amplification of pET-PM by PCR, where M: 1 kb DNA Ladder, 1: PCR product, and 2: pET-PM (control).
Figure 18:
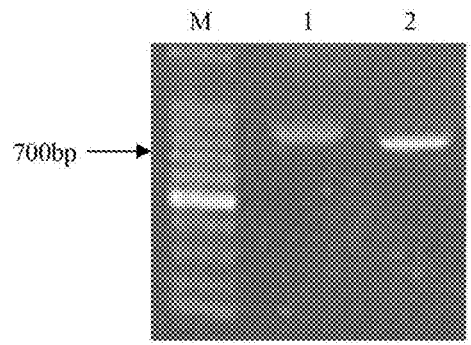
FIG. 18 shows the result of electrophoresis after amplification of EGFP and a linker by overlap PCR, where M: 100 bp DNA Ladder, 1: linker+EGFP, and 2: EGFP (control).

The three amplified DNA fragments were each obtained by agarose gel electrophoresis and excision purification. Subsequently, overlap PCR using the two inserts as templates was performed using EGFP_XhoI_For and Age_P2GSCGS_Back. In also this case, after the PCR, agarose gel electrophoresis and excision purification were performed. Finally, the vectors and the inserts were fused by In-fusion reaction. The outline of construction of a plasmid is shown in FIG. 16. After transformation using the resulting plasmid into XL10-Gold and culturing, the plasmid was extracted and subjected sequence analysis.
II Results and Consideration
FIG. 17 shows the result of agarose gel electrophoresis after amplification of pET-PM by PCR. Acquisition of the target vector was confirmed by this result. In addition, FIG. 18 shows the result of agarose gel electrophoresis after amplification of EGFP and a linker and overlap PCR amplification of the both. DNA having a molecular weight larger than that of the band of EGFP only as a control was observed. The result of sequence analysis of pET32-PMEGFP prepared by fusion of a vector and an insert through In-fusion reaction is shown as SEQ ID NO: 16. Acquisition of pET32-PMEGFP was confirmed by the result.

[Example 9] Production and Evaluation of PMEGFP Probe 1.1 Experimental Procedure
1.1.1 Protein Expression
An objective plasmid (1 μL) was added to *E. coli* SHuffle T7 Express LysY for expressing a protein (20 μL, New England Biolabs Japan Inc.), and heat shock was performed at 42° C. for 1 minute. After leaving to stand on ice for 1 minute, 200 μL of an SOC medium was added thereto, followed by incubation at 30° C. Subsequently, 20 μL of the medium was seeded on an LBA agar medium, followed by culturing at 30° C. overnight. On the following day, a single colony was inoculated in 4 mL of an LBA liquid medium and was cultured with shaking at 30° C. overnight. The total volume (4 mL) of the cultured *E. coli* was added to 400 mL of an LBA liquid medium and cultured at 30° C. until the OD reaches 0.6 to 0.8, and IPTG was added thereto to be 0.4 mM for inducing protein expression. The protein was expressed by shaking culture at 16° C. overnight.

1.1.2 Purification of Protein by His-Tag

The plasmid used in this example contained His×6. In order to recognize this sequence and purify His-tag fusion protein, immobilized metal affinity chromatography (IMAC) purification was performed using a TALON (registered trademark) Metal Affinity Resin (Clontech Laboratories, Inc.). The procedure was as follows:

1) Dispense 200 mL aliquots of the *E. coli* culture solution prepared by shaking culture into 500-mL tubes, centrifuge at 4° C. at 5000×g for 20 minutes, and remove the supernatant;
2) Suspend the pellet in 5 mL of a phosphate buffer (containing NaCl) (hereinafter referred to as PB) and disrupt the cells with a cell crushing apparatus (Constant Systems Ltd.);
3) Centrifuge at 4° C. at 8000×g for 10 minutes and collect the supernatant;
4) Here, 200 μL (bed volume: 100 μL) of TALON (registered trademark) Metal Affinity Resin beads (Clontech Laboratories, Inc.) are prepared. The beads are transferred to a 1.5-mL tube and are centrifuged at 4° C. at 100×g, and the supernatant is then removed. Addition of 500 μL of PB, centrifugation, and removal of the supernatant are repeated three times to wash the beads;
5) Add the beads in step 4) to the supernatant in step 3) and rotate with a mini rotary mixer NRC-20D (NISSIN) at room temperature for 1 hour;
6) Centrifuge at 4° C. at 100×g for 1 minute and remove the supernatant;
7) Transfer the beads to TALON (registered trademark) 2-mL Disposable Gravity Column (Takara Bio Inc.) and discharge the supernatant;
8) Add 500 μL of His Spin Trap binding buffer three times to wash the beads; and
9) Add 200 μL of His Spin Trap elution buffer to elute the target protein and collect the protein in a 1.5-mL tube.

1.1.3 Buffer Displacement by Illustra™ Microspin™ G-25 Column

Imidazole contained in an elution buffer may deactivate protein and is not suitable for long storage of samples. In addition, imidazole is also used to elute the target protein in the subsequent modification with a fluorescent dye, imidazole should be removed at this time. Accordingly, the buffer after the protein purification was changed to PBS using an Illustra™ Microspin™ G-25 Column (GE Healthcare). The procedure was as follows:

1) Resuspend the inside of the column, then remove the lower lid, set the column to a 2-mL tube with the upper lid loosened, centrifuge at 735×g at room temperature for 1 minute, and then remove the stock solution;
2) Add 200 μL of PBS for resuspension, centrifuge at 735×g at room temperature for 1 minute, and then remove the washing solution; and
3) Set the column to a 1.5-mL tube, add about 200 μL of a sample, centrifuge at 735×g at room temperature for 1 minute, and then collect the sample.

TABLE 1

| PBS (pH 7.4) | |
|---|---|
| NaCl | 137 mM |
| KCl | 270 μM |
| Na$_2$HPO$_4$ | 10.1 mM |
| KH$_2$PO$_4$ | 1.7 mM |
| Phosphate Buffer (+NaCl) pH 7.4 | |
| Na$_2$HPO$_4$ | 20 mM |
| NaH$_2$PO$_4$ | 20 mM |
| NaCl | 500 mM |
| His Spin Trap binding buffer pH 7.4 | |
| Phosphate buffer | 20 mM |
| NaCl | 500 mM |
| Imidazole | 20 mM |
| His Spin Trap binding buffer pH 7.4 | |
| Phosphate buffer | 20 mM |
| NaCl | 500 mM |
| Imidazole | 500 mM |

1.1.4 SDS-PAGE

In order to verify whether the purified protein was the target material or not, SDS-PAGE was performed. DTT was added to 1 to 2 μg of the protein, followed by heating at 95° C. for 5 minutes for denaturation. Subsequently, the protein solution was applied to a well and was subjected to electrophoresis. Staining after the electrophoresis was performed with coomassie brilliant blue (CBB). Specifically, shaking immersion was performed in a fixing solution, a stain solution, and Milli-Q water in this order for 30 minutes each.

1.1.5 Labeling with Fluorescent Dye

The resulting protein was modified with a fluorescent dye. In this example, 5(6)-TAMRA C6-maleimide (AAT Bioquest, Inc.) was used as the fluorescent dye. This fluorescent dye was mixed with the protein. Consequently, the Cys residue present in the protein and the fluorescent dye caused a maleimide-thiol reaction and bound to each other.

A mixture adjusted to 0.5 nmol of the protein and 2.5 mM TCEP was rotated at room temperature for 30 minutes for reduction of Cys residue. Subsequently, 4-azidobenzoic acid (Tokyo Chemical Industry Co., Ltd.) was added to be 10 mM. After leaving to stand on ice for 10 minutes, 5(6)-TAMRA C6-maleimide was added to be 50 μM, followed by rotation with shielding light for 2 hours. After the reaction, the protein was purified with a His Spin Trap column (GE Healthcare) to remove unreacted fluorescent dye. The procedure was as follows:

1) Suspend the solution in the column, put the column in a 2-mL tube, centrifuge at 4° C. at 100×g for 30 seconds, and remove the filtrate;
2) Add 600 μL of a binding buffer to the column, centrifuge at 4° C. at 100×g for 30 seconds, and remove the filtrate;
3) Add the protein solution, centrifuge at 4° C. at 100×g for 30 seconds, and remove the filtrate;
4) Add 600 μL of a binding buffer, centrifuge at 4° C. at 100×g for 30 seconds, and remove the filtrate, which was washing operation and was repeated ten times to remove unreacted fluorescent dye as much as possible;
5) Put the column in a 1.5-mL tube, add 200 μL of an elution buffer, and leave to stand on ice for 5 minutes with tapping; and
6) Centrifuge at 4° C. at 100×g for 30 seconds to elute the protein.

The protein concentration after elution was measured by SDS-PAGE.

1.1.6 Fluorescence Measurement

Fluorescence measurement used FP-8500 fluorescence spectrophotometer (JASCO Corporation). Excitation light having a wavelength suitable for the fluorescent dye and the fluorescence protein was irradiated, and the resulting change in the fluorescence intensity was measured. The measurement conditions were as follows:

Temperature: 25° C.,
Excitation band width: 5 nm,
Fluorescence band width: 5 nm,
Scanning speed: 500 nm/min,
Response: 2 sec,
Sensitivity: High, and
Excitation wavelength and measurement wavelength: described in each experiment.

A protein probe (250 µL) was added to each of four quartz microcells having an optical path length of 5×5 mm. In addition, simultaneously, a stirrer was placed in each microcell and stirred the solution for homogenization during measurement. To three of the four microcells, an antibody or a Fab fragment and an antigen were further added sequentially. Fluorescence was measured after each addition. Instead of the above-mentioned addition, the same amount of PBST was added to the remaining one microcell as a control, followed by measurement to verify the changes in fluorescence intensity due to dilution and discoloration of the fluorescent dye. The measurement was performed 20 minutes or more after the addition of each solution to the microcell.

1.2 Protein Expression of Each Probe and Fluorescent Dye Modification pET32-PMEGFP was transformed into SHuffle T7 Express lysY, and after culturing, IMAC purification using Talon beads was performed. Subsequently, each probe was modified with a fluorescent dye TAMRA C6, and the modification was verified by SDS-PAGE.

1.3 Fluorescence Measurement of Each Probe Using BGP Peptide

Each of the TAMRA C6-modified probes was diluted with PBST to 5 nM and was put in a cell, and the fluorescence was measured. Subsequently, a mouse/human chimera (composed of a mouse-derived variable region sequence and a human IgG1-derived constant region sequence) or a Fab fragment of anti-BGP mouse antibody (BGP Fab) and BGP-C7 were sequentially added, followed by measurement 20 minutes after the respective additions. The changes in the fluorescence intensity of three prepared probes were compared using an excitation wavelength of 460 nm and a fluorescence wavelength of 500 to 600 nm.

II Experimental Results and Consideration

2.1 Protein Expression of Each Probe and Fluorescent Dye Modification

Figure 19:
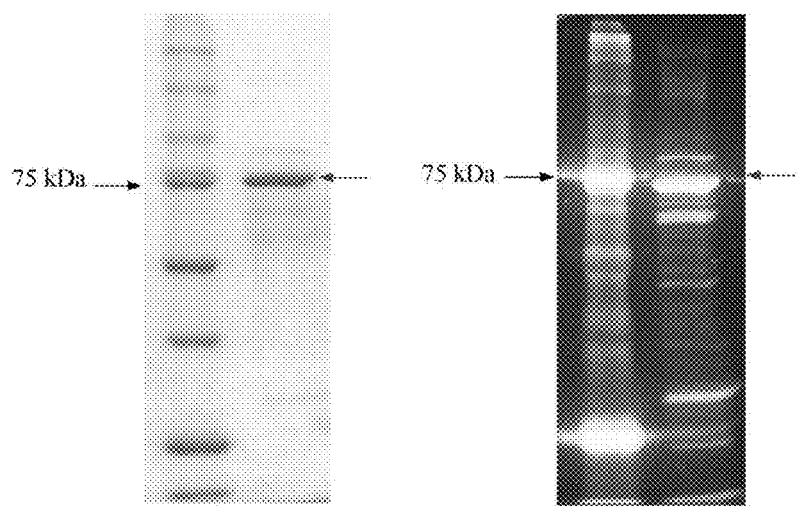
FIG. 19 shows the results of electrophoresis of fluorescence-labeled PM-EGFP.

FIG. 19 shows the results of SDS-PAGE of fluorescence-labeled PM-EGFP (about 90 kDa). The result demonstrated acquisition of each probe.

2.2 Fluorescence Measurement of Each Probe Using BGP Peptide

Figure 20:
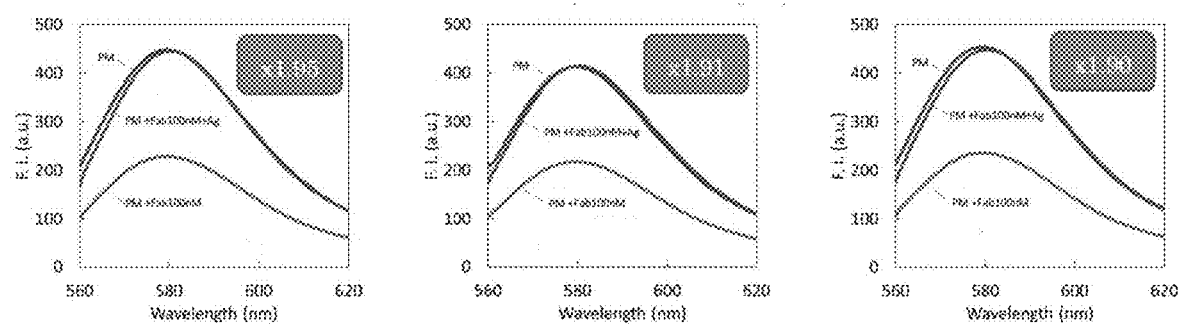
FIG. 20 includes graphs showing the results of measurement of fluorescence of a protein M probe, where protein M (PM): 5 nM, anti-BGP antibody Fab fragment (human Fab): 100 nM, antigen (BGP-C7:Ag): 1 µM. The experiment was performed three times under the same conditions, and the results thereof are shown in the three graphs. The numerical value on the upper right of each graph is a relative value of the maximum fluorescence intensity at the time of addition of the antigen relative to the maximum fluorescence intensity at the time of quenching defined as 1.
Figure 21:
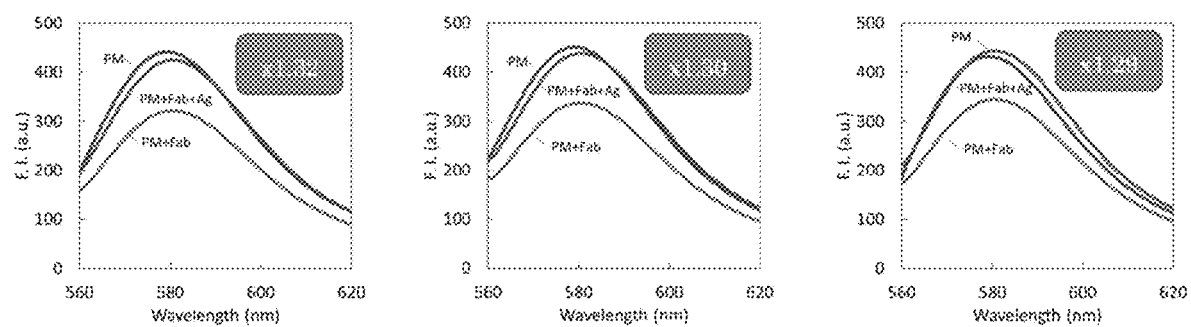
FIG. 21 includes graphs showing the results of measurement of fluorescence of a protein M probe, where protein M (PM): 5 nM, anti-BGP antibody Fab fragment (mouse Fab): 350 nM, antigen (BGP-C7:Ag): 1 fM. The experiment was performed three times under the same conditions, and the results thereof are shown in the three graphs. The numerical value on the upper right of each graph is a relative value of the maximum fluorescence intensity at the time of addition of the antigen relative to the maximum fluorescence intensity at the time of quenching defined as 1.
Figure 22:
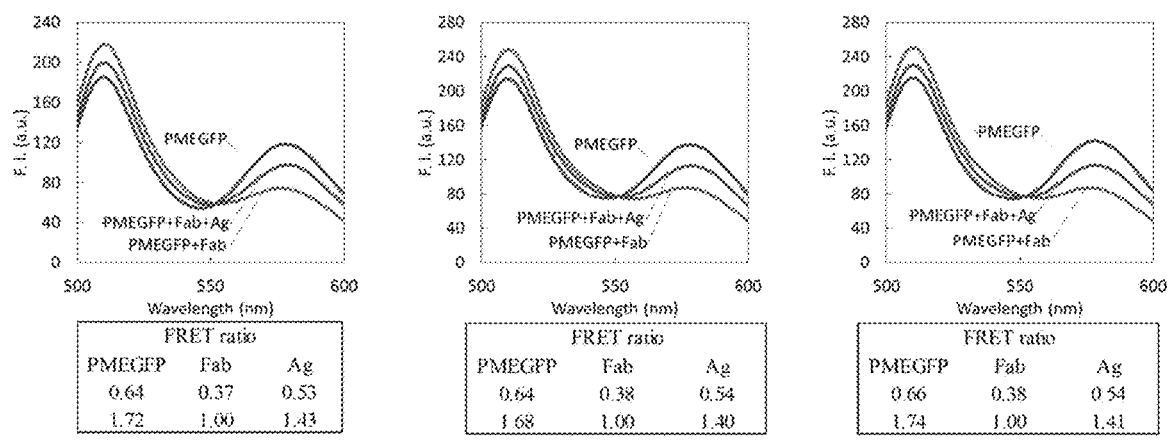
FIG. 22 includes graphs showing the results of measurement of fluorescence of an EGFP-binding protein M probe, where EGFP-binding protein M (PMEGPF): 5 nM, anti-BGP antibody Fab fragment (mouse Fab): 550 nM, antigen (BGP-C7:Ag): 1 µM. The experiment was performed three times under the same conditions, and the results thereof are shown in the three graphs. In the numerical values shown under each graph, the numerical values on the upper row are the fluorescence intensity ratios (fluorescence intensity at 580 nm/fluorescence intensity at 515 nm) before the addition of the Fab fragment (PMEGFP), at the time of addition of the Fab fragment (Fab), and at the time of addition of the antigen (Ag); and the numerical values on the lower row are relative values of the fluorescence intensity ratios shown on the upper row relative to the fluorescence intensity ratio at the time of addition of the Fab fragment defined as 1. The fluorescence intensity ratio was changed to by about 1.4 times by addition of the antigen.

FIGS. 20 to 22 show the results of fluorescence measurement of each of the TAMRA C6-modified probes. FIGS. 20 and 21 show the results when protein M was used as the probe. FIG. 22 shows the results when EGFP-binding protein M was used as the probe.

As shown in FIG. 22, even when the EGFP-binding protein M was used, quenching (at the time of addition of the Fab fragment) at around 580 nm (the fluorescence wavelength of TAMRA C6) and release of quenching (at the time of addition of the antigen) were observed, as in the case of using protein M. In contrast, at around 515 nm, which is the fluorescence wavelength of EGFP, a decrease in the fluorescence intensity due to FRET was observed at the time of addition of the antigen.

A mouse/human chimera anti-BGP antibody Fab fragment (FIGS. 20 and 22) and an anti-BGP mouse antibody Fab fragment (FIG. 21) were used as the Fab fragments. The decrease in the fluorescence intensity when the anti-BGP mouse antibody Fab fragment was added was smaller than that when the mouse/human chimera anti-BGP antibody Fab fragment was added.

All publications, patents, and patent applications cited herein are incorporated herein by reference in their entirety.

INDUSTRIAL APPLICABILITY

The present invention can be usefully used in, for example, the field of sample analysis and drug testing or the field of portable sample analysis kits.

---

The invention claimed is:

1. A method for detecting an antigen or measuring an amount of the antigen in a sample, comprising sequentially performing steps (1) to (3):
    (1) bringing a sample into contact with a complex composed of a polypeptide including an antibody light chain variable region and a polypeptide including an antibody heavy chain variable region in the presence of a protein M fragment labeled with a fluorescent dye, wherein the protein M fragment is a fragment consisting of residues 78-468 of protein M having a binding ability to the complex;
    (2) measuring the fluorescence intensity of the fluorescent dye; and
    (3) judging presence of the antigen in the sample from the fluorescence intensity or calculating the antigen level in the sample from the fluorescence intensity,
    wherein the complex composed of a polypeptide including an antibody light chain variable region and a polypeptide including an antibody heavy chain variable region is a full-length antibody.

2. The method for detecting the antigen or measuring the amount of the antigen according to claim 1, wherein the fluorescent dye labels the C-terminal side of the protein M fragment.

3. The method for detecting the antigen or measuring the amount of the antigen according to claim 1, wherein the protein M fragment is labeled with two fluorescent dyes.

4. The method for detecting the antigen or measuring the amount of the antigen according to claim 3, wherein the two fluorescent dyes are a rhodamine dye and green fluorescent protein (GFP) or a variant thereof.

* * * * *